US012773282B2

(12) United States Patent
Chappuis et al.

(10) Patent No.: US 12,773,282 B2
(45) Date of Patent: Oct. 27, 2026

(54) SURGICAL ROBOT WITH PASSIVE END EFFECTOR

(71) Applicant: GLOBUS MEDICAL, INC., Audubon, PA (US)

(72) Inventors: Olivier Chappuis, Lutry (CH); Szymon Kostrzewski, Lausanne (CH)

(73) Assignee: Globus Medical, Inc., Audubon, PA (US)

( * ) Notice: Subject to any disclaimer, the term of this patent is extended or adjusted under 35 U.S.C. 154(b) by 456 days.

(21) Appl. No.: 18/409,213

(22) Filed: Jan. 10, 2024

(65) Prior Publication Data

US 2024/0180637 A1 Jun. 6, 2024

Related U.S. Application Data

(63) Continuation of application No. 16/587,203, filed on Sep. 30, 2019, now Pat. No. 11,890,066.

(51) Int. Cl.

| | |
|---|---|
| ***A61B 34/30*** | (2016.01) |
| ***A61B 17/14*** | (2006.01) |
| ***A61B 90/00*** | (2016.01) |
| *A61B 17/00* | (2006.01) |

(Continued)

(52) U.S. Cl.

CPC .............. *A61B 34/30* (2016.02); *A61B 17/14* (2013.01); *A61B 90/37* (2016.02); *A61B 2017/00477* (2013.01); *A61B 2017/00991* (2013.01); *A61B 2034/2072* (2016.02); *A61B 2090/364* (2016.02); *A61B 2090/502* (2016.02)

(58) Field of Classification Search

CPC ......... A61B 34/30; A61B 90/37; A61B 17/14; A61B 2034/2072; A61B 2090/364; A61B 2090/502; A61B 2017/00477; A61B 2017/00991

See application file for complete search history.

(56) References Cited

U.S. PATENT DOCUMENTS

| | | | |
|---|---|---|---|
| 1,068,626 | A | 7/1913 | Buck |
| 4,150,293 | A | 4/1979 | Franke |
| 4,737,038 | A | 4/1988 | Dostoomian |

(Continued)

FOREIGN PATENT DOCUMENTS

| | | | |
|---|---|---|---|
| CN | 104173091 | A | 12/2014 |
| CN | 108175507 | A | 6/2018 |

(Continued)

OTHER PUBLICATIONS

US 8,231,638 B2, 07/2012, Swarup et al. (withdrawn)

*Primary Examiner* — Sameh R Boles

(57) ABSTRACT

A passive end effector of a surgical system includes a base, a first mechanism, and a second mechanism. The base attaches to an end effector coupler of a robot arm positioned by a surgical robot. The first mechanism extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections to constrain movement of the tool attachment mechanism to a range of movement within a working plane. The tool attachment mechanism is configured to connect to a surgical saw including a saw blade for cutting.

20 Claims, 17 Drawing Sheets

(51) Int. Cl.
*A61B 34/20* (2016.01)
*A61B 90/50* (2016.01)

(56) References Cited

U.S. PATENT DOCUMENTS 4,757,710 A 7/1988 Haynes
5,246,010 A 9/1993 Gazzara et al.
5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.

(56) References Cited

U.S. PATENT DOCUMENTS 7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.

(56) References Cited

U.S. PATENT DOCUMENTS 8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Issacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Tott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,005,113 B2 4/2015 Scott et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,271,633 B2 3/2016 Scott et al.
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,565,997 B2 2/2017 Scott et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
9,962,069 B2 5/2018 Scott et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.

(56) References Cited

U.S. PATENT DOCUMENTS

2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 von Jako
2008/0109012 A1 5/2008 Falco et al.
2008/0144906 A1 6/2008 Allred et al.
2008/0161680 A1 7/2008 von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0082587 A1 4/2011 Ziaei et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.

(56) References Cited

U.S. PATENT DOCUMENTS

| | | | |
|---|---|---|---|
| 2014/0088612 A1 | 3/2014 | Bartol et al. | |
| 2014/0094694 A1 | 4/2014 | Moctezuma de la Barrera | |
| 2014/0094851 A1 | 4/2014 | Gordon | |
| 2014/0096369 A1 | 4/2014 | Matsumoto et al. | |
| 2014/0100587 A1 | 4/2014 | Farritor et al. | |
| 2014/0121676 A1 | 5/2014 | Kostrzewski et al. | |
| 2014/0128882 A1 | 5/2014 | Kwak et al. | |
| 2014/0130810 A1 | 5/2014 | Azizian et al. | |
| 2014/0135796 A1 | 5/2014 | Simon et al. | |
| 2014/0142591 A1 | 5/2014 | Alvarez et al. | |
| 2014/0142592 A1 | 5/2014 | Moon et al. | |
| 2014/0148692 A1 | 5/2014 | Hartmann et al. | |
| 2014/0163581 A1 | 6/2014 | Devengenzo et al. | |
| 2014/0171781 A1 | 6/2014 | Stiles | |
| 2014/0171900 A1 | 6/2014 | Stiles | |
| 2014/0171965 A1 | 6/2014 | Loh et al. | |
| 2014/0180308 A1 | 6/2014 | von Grunberg | |
| 2014/0180309 A1 | 6/2014 | Seeber et al. | |
| 2014/0187915 A1 | 7/2014 | Yaroshenko et al. | |
| 2014/0188132 A1 | 7/2014 | Kang | |
| 2014/0194699 A1 | 7/2014 | Roh et al. | |
| 2014/0221819 A1 | 8/2014 | Sarment | |
| 2014/0222023 A1 | 8/2014 | Kim et al. | |
| 2014/0228631 A1 | 8/2014 | Kwak et al. | |
| 2014/0234804 A1 | 8/2014 | Huang et al. | |
| 2014/0257328 A1 | 9/2014 | Kim et al. | |
| 2014/0257329 A1 | 9/2014 | Jang et al. | |
| 2014/0257330 A1 | 9/2014 | Choi et al. | |
| 2014/0275760 A1 | 9/2014 | Lee et al. | |
| 2014/0275985 A1 | 9/2014 | Walker et al. | |
| 2014/0276931 A1 | 9/2014 | Parihar et al. | |
| 2014/0276940 A1 | 9/2014 | Seo | |
| 2014/0276944 A1 | 9/2014 | Farritor et al. | |
| 2014/0288413 A1 | 9/2014 | Hwang et al. | |
| 2014/0299648 A1 | 10/2014 | Shelton, IV et al. | |
| 2014/0303434 A1 | 10/2014 | Farritor et al. | |
| 2014/0303643 A1 | 10/2014 | Ha et al. | |
| 2014/0305995 A1 | 10/2014 | Shelton, IV et al. | |
| 2014/0309659 A1 | 10/2014 | Roh et al. | |
| 2014/0316436 A1 | 10/2014 | Bar et al. | |
| 2014/0323803 A1 | 10/2014 | Hoffman et al. | |
| 2014/0324070 A1 | 10/2014 | Min et al. | |
| 2014/0330288 A1 | 11/2014 | Date et al. | |
| 2014/0364720 A1 | 12/2014 | Darrow et al. | |
| 2014/0371577 A1 | 12/2014 | Maillet et al. | |
| 2015/0039034 A1 | 2/2015 | Frankel et al. | |
| 2015/0085970 A1 | 3/2015 | Bouhnik et al. | |
| 2015/0146847 A1 | 5/2015 | Liu | |
| 2015/0150524 A1 | 6/2015 | Yorkston et al. | |
| 2015/0196261 A1 | 7/2015 | Funk | |
| 2015/0213633 A1 | 7/2015 | Chang et al. | |
| 2015/0335480 A1 | 11/2015 | Alvarez et al. | |
| 2015/0342647 A1 | 12/2015 | Frankel et al. | |
| 2016/0005194 A1 | 1/2016 | Schretter et al. | |
| 2016/0166329 A1 | 6/2016 | Langan et al. | |
| 2016/0235480 A1 | 8/2016 | Scholl et al. | |
| 2016/0249990 A1 | 9/2016 | Glozman et al. | |
| 2016/0302871 A1 | 10/2016 | Gregerson et al. | |
| 2016/0320322 A1 | 11/2016 | Suzuki | |
| 2016/0331335 A1 | 11/2016 | Gregerson et al. | |
| 2017/0135770 A1 | 5/2017 | Scholl et al. | |
| 2017/0143284 A1 | 5/2017 | Sehnert et al. | |
| 2017/0143426 A1 | 5/2017 | Isaacs et al. | |
| 2017/0156816 A1 | 6/2017 | Ibrahim | |
| 2017/0202629 A1 | 7/2017 | Maillet et al. | |
| 2017/0212723 A1 | 7/2017 | Atarot et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0231710 A1 | 8/2017 | Scholl et al. | |
| 2017/0258426 A1 | 9/2017 | Risher-Kelly et al. | |
| 2017/0273748 A1 | 9/2017 | Hourtash et al. | |
| 2017/0296277 A1 | 10/2017 | Hourtash et al. | |
| 2017/0360493 A1 | 12/2017 | Zucher et al. | |
| 2018/0228351 A1 | 8/2018 | Scott et al. | |
| 2021/0369359 A1* | 12/2021 | Blanckaert | A61B 34/77 |

FOREIGN PATENT DOCUMENTS

| | | | |
|---|---|---|---|
| EP | 0104732 | A1 | 4/1984 |
| EP | 2821023 | A1 | 1/2015 |
| JP | 2019-520859 | A | 7/2019 |
| WO | 2017160889 | A1 | 9/2017 |
| WO | 2018104523 | A1 | 6/2018 |
| WO | 2019141704 | A1 | 7/2019 |

* cited by examiner

SURGICAL ROBOT WITH PASSIVE END EFFECTOR

CROSS-REFERENCE TO RELATED APPLICATION(S)

The present application is a continuation of U.S. patent application Ser. No. 16/587,203, filed on Sep. 30, 2019 (published as U.S. Pat. Pub. No. 2021-0093396), the entire contents of which is incorporated herein by reference in its entirety for all purposes.

FIELD

The present disclosure relates to medical devices and systems, and more particularly, robotic systems and related end effectors for controlling cutting of anatomical structures of a patient, and related methods and devices.

BACKGROUND

There are a number of surgical interventions requiring osteotomy, i.e. cutting an anatomical structure such as a bone along a target plane. Total knee arthroplasty typically requires cutting both the femoral epiphysis and tibial epiphysis in order to remove the damaged bone and cartilage and install a knee prosthesis. A surgeon may perform five or more cuts on the femur and one or more cuts on the tibia using an oscillating surgical saw.

During orthopedic surgeries, including joints and knees, it is important to accurately align and stabilize the saw while cutting a desired location on a bone. The surgeon's limited visibility to the surgical site combined with the difficultly in controlling movement of the saw creates a risk that an undesired part of a bone or adjacent tissue becomes cut. Vibrations generated by the saw while cutting can reduce the accuracy of the cuts. During knee surgery, the precision of a bone cut (planar cuts) affects how precisely the implant can be connected to the exposed bone.

During some knee surgeries, a jig is screwed to a bone for guiding a surgeon's movement of a saw while cutting. Error in jig placement and limited stability of the saw blade during cutting can limit precision of the cuts. Moreover, contact between the saw blade and the jig can generate debris which risks entering the patient.

SUMMARY

Some embodiments of the present disclosure are directed to a passive end effector of a surgical system. The passive end effector includes a base, a first mechanism, and a second mechanism. The base is configured to attach to an end effector coupler of a robot arm positioned by a surgical robot. The first mechanism extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections to constrain movement of the tool attachment mechanism to a range of movement within a working plane. The tool attachment mechanism is configured to connect to a surgical saw including a saw blade for cutting.

In some further embodiments, the surgical system further includes a tracking system that is configured to determine a pose of an anatomical structure that is to be cut by the saw blade and to determine a pose of the saw blade. The surgical robot includes a robot base, at least one motor, and at least one controller. The robot arm is connected to the robot base and configured to position the passive end effector. The at least one motor is operatively connected to move the robot arm relative to the robot base. The at least one controller is connected to the at least one motor and configured to determine a pose of the target plane based on a surgical plan defining where the anatomical structure is to be cut and based on the pose of the anatomical structure. The at least one controller is further configured to generate steering information based on comparison of the pose of the target plane and the pose of the surgical saw, and where the steering information indicates where the passive end effector needs to be moved to position the working plane of the passive end effector so the cutting plane of the saw blade is aligned with the target plane.

In a first embodiment of the passive end effector, the first mechanism includes first and second link segments, where the first link segment extends between a rotatable connection to a first location on the base and a rotatable connection to an end of the second link segment. The second mechanism includes third and fourth link segments, where the third link segment extends between a rotatable connection to a second location on the base and a rotatable connection to an end of the fourth link segment, and where the first and second locations on the base are spaced apart on opposite sides of a rotational axis of the base when rotated by the robot arm. The tool attachment mechanism includes a fifth link segment that extends between rotatable connections to distal ends of the second and fourth link segments from the base.

In a second embodiment of the passive end effector, the first mechanism includes first and second link segments, where the first link segment extends between a rotatable connection to a first location on the base and a rotatable connection to an end of the second link segment. The second mechanism includes third and fourth link segments, where the third link segment extends between a rotatable connection to a second location on the base and a rotatable connection to an end of the fourth link segment, where the first and second locations on the base are spaced apart on opposite sides of a rotational axis of the base when rotated by the robot arm. The distal ends of the second and fourth link segments from the base are rotatably connected to each other and to the tool attachment mechanism.

In a third embodiment of the passive end effector, the base includes first and second elongated base segments that extend from spaced apart locations on opposite sides of a rotational axis of the base when rotated by the robot arm, and the first and second elongated base segments extend in a direction away from the end effector coupler of the robot arm when attached to the passible end effector. The first mechanism includes first, second, third, and fourth link segments, where the first and second link segments extend parallel to each other between rotatable connections to spaced apart locations on the first elongated base segment and spaced apart locations on the third link segment. An end of the third link segment is rotatably connected to an end of the fourth link segment. The second mechanism includes fifth, sixth, and seventh link segments, where the fifth and sixth link segments extend parallel to each other between rotatable connections to spaced apart locations on the second elongated base segment and spaced apart locations on the seventh link segment. The tool attachment mechanism includes an eighth link segment that extends between rotatable connections to distal ends of the fourth and seventh link segments from the base.

In a fourth embodiment of the passive end effector, the first mechanism includes a first link segment. The second mechanism includes a second link segment. The tool attachment mechanism includes third, fourth, fifth, sixth, and seventh link segments. The first and second link segments extend between rotatable connections to first and second locations, respectively, on the base to rotatable connections at opposite ends of the third link segment. The first and second locations on the base are spaced apart on opposite sides of a rotational axis of the base when rotated by the robot arm. The fourth link segment extends from the third link segment in a direction towards the base. The fifth and sixth link segments extend parallel to each other between rotatable connections to spaced apart locations on the fourth link segment and spaced apart locations on the seventh link segment. The seventh link segment includes a rotatable connector that is configured to connect to the surgical saw.

In fifth embodiment of the passive end effector, the first mechanism includes a first link segment. The second mechanism includes a second link segment. The tool attachment mechanism includes third, fourth, fifth, sixth, and seventh link segments. The first and second link segments extend between rotatable connections to first and second locations, respectively, on the base to rotatable connections at opposite ends of the third link segment. The first and second locations on the base are spaced apart on opposite sides of a rotational axis of the base when rotated by the robot arm. The fourth link segment extends from the third link segment in a direction away from the base. The fifth and sixth link segments extend parallel to each other between rotatable connections to spaced apart locations on the fourth link segment and spaced apart locations on the seventh link segment. The seventh link segment includes a rotatable connector that is configured to connect to the surgical saw.

In a sixth embodiment of the passive end effector, the first mechanism includes first and second link segments, where the first link segment extends between a rotatable connection to the base and a rotatable connection to an end of the second link segment. The second mechanism includes a third link segment. The tool attachment mechanism includes a fourth link segment, where the second and third link segments extend away from the base and parallel to each other between rotatable connections to spaced apart locations on the first link segment and spaced apart locations on the fourth link segment. The fourth link segment includes an attachment member that extends in a direction away from the base to a rotatable connector that is configured to connect to the surgical saw. The attachment member extends from a location on the fourth link segment that is closer to the third link segment than to the second link segment.

In a seventh embodiment of the passive end effector, the first mechanism includes a first link segment, and the second mechanism includes a second link segment. The tool attachment mechanism includes a third link segment. The first and second link segments extend between rotatable connections to first and second locations, respectively, on the base to rotatable connections at opposite ends of the third link segment. The first and second locations on the base are spaced apart on opposite sides of a rotational axis of the base when rotated by the robot arm. The third link segment includes an attachment member that extends in a direction away from the base to a rotatable connector that is configured to connect to the surgical saw. The attachment member extends from a location on the third link segment that is closer to the first link segment than to the second link segment.

Some other embodiments of the present disclosure are directed to a surgical system that includes a tracking system, a surgical robot, and a passive end effector. The tracking system is configured to determine a pose of an anatomical structure that is to be cut by a saw blade and to determine a pose of the saw blade. The surgical robot includes a robot base, a robot arm connected to the robot base, and at least one motor operatively connected to move the robot arm relative to the robot base. The passive end effector includes a base, a first mechanism, and a second mechanism. The base is configured to attach to an end effector coupler of the robot arm. The first mechanism that extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections which may be configured to constrain movement of the tool attachment mechanism to a range of movement within a working plane. The tool attachment mechanism is configured to connect to the surgical saw comprising a saw blade configured for cutting. The first and second mechanisms may constrain a cutting plane of the saw blade to be parallel to the working plane. The surgical robot further includes at least one controller connected to the at least one motor and configured to determine a pose of the target plane based on a surgical plan defining where the anatomical structure is to be cut and based on the pose of the anatomical structure, and generate steering information based on comparison of the pose of the target plane and the pose of the surgical saw. The steering information indicates where the passive end effector needs to be moved so the cutting plane of the saw blade becomes aligned with the target plane and the saw blade becomes positioned a distance from the anatomical structure to be cut that is within the range of movement of the tool attachment mechanism of the passive end effector.

Other surgical systems, passive end effectors, and corresponding methods and computer program products according to embodiments will be or become apparent to one with skill in the art upon review of the following drawings and detailed description. It is intended that all such surgical systems, passive end effectors, and corresponding methods and computer program products be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Figure 1:
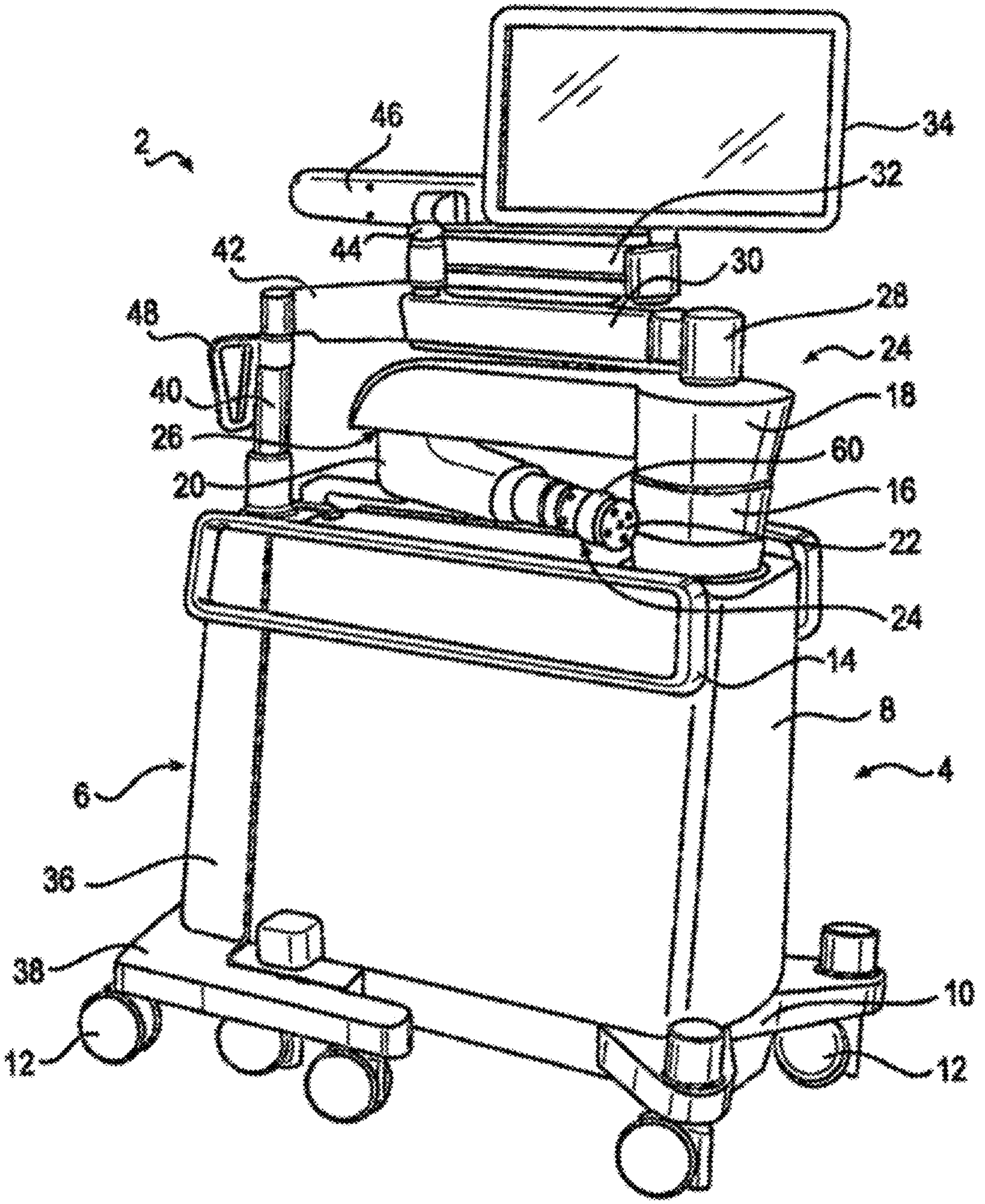
FIG. 1 illustrates an embodiment of a surgical system according to some embodiments of the present disclosure.

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Various embodiments disclosed herein are directed to improvements in operation of a surgical system when performing surgical interventions requiring osteotomy. Passive end effectors are disclosed that are connectable to a robot arm positioned by a surgical robot. The passive end effectors have pairs of mechanisms that constrain movement of a tool attachment mechanism to a range of movement. The tool attachment is connectable to a surgical saw for cutting, such as a sagittal saw having an oscillating saw blade. The mechanisms may be configured to constrain a cutting plane of the saw blade to be parallel to the working plane. The surgical robot can determine a pose of the target plane based on a surgical plan defining where an anatomical structure is to be cut and based on a pose of the anatomical structure, and can generate steering information based on comparison of the pose of the target plane and the pose of the surgical saw. The steering information indicates where the passive end effector needs to be moved so the cutting plane of the saw blade becomes aligned with the target plane and the saw blade becomes positioned a distance from the anatomical structure to be cut that is within the range of movement of the tool attachment mechanism of the passive end effector.

These and other related embodiments can operate to improve the precision of the guidance of the saw blade compared to other robotic and manual (e.g., jigs) solutions for surgeries. The mechanisms of the passive end effector can allow the surgeon to concentrate on interpreting the direct force feedback while cutting bones using a surgical saw that is guided by the passive end effector. The mechanisms may be planar mechanism, e.g., having 1 degree of freedom end joint that is configured to constrain the cutting plane to be aligned with the target plane. The surgeon may also more accurately monitor and control the speed of bone removal based on audio and/or visual notification feedback provided through the surgical robot.

These embodiments can provide guidance during joint surgeries and especially knee surgery with high precision, high rigidity, sufficient workspace and direct force feedback. As will be explained in detail below, a tracking system can be used to precisely align the cutting plane with the target plane for cutting a bone. High precision cuts may be achieved by the planar mechanisms constraining the cutting plane to remaining aligned with the target plane while a surgeon moves the saw blade along the cutting plane and directly senses force feedback of the saw blade cutting bone. Moreover, these embodiments can be rapidly deployed into surgical practices through defined changes in existing accepted surgery workflows.

FIG. 1 illustrates an embodiment of a surgical system 2 according to some embodiments of the present disclosure. Prior to performance of an orthopedic surgical procedure, a three-dimensional ("3D") image scan may be taken of a planned surgical area of a patient using, e.g., the C-Arm imaging device 104 of FIG. 10 or O-Arm imaging device 106 of FIG. 11, or from another medical imaging device such as a computed tomography (CT) image or MRI. This scan can be taken pre-operatively (e.g. few weeks before procedure, most common) or intra-operatively. However, any known 3D or 2D image scan may be used in accordance with various embodiments of the surgical system 2. The image scan is sent to a computer platform in communication with the surgical system 2, such as the surgical system computer platform 900 of FIG. 9 which includes the surgical robot 800 (e.g., robot 2 in FIG. 1) and a surgical planning computer 910. A surgeon reviewing the image scan(s) on a display device of the surgical planning computer 910 (FIG. 9) generates a surgical plan defining a target plane where an anatomical structure of the patient is to be cut. This plane is a function of patient anatomy constraints, selected implant and its size. In some embodiments, the surgical plan defining the target plane is planned on the 3D image scan displayed on a display device.

The surgical system 2 of FIG. 1 can assist surgeons during medical procedures by, for example, holding tools, aligning tools, using tools, guiding tools, and/or positioning tools for use. In some embodiments, surgical system 2 includes a surgical robot 4 and a camera tracking system 6. Both systems may be mechanically coupled together by any various mechanisms. Suitable mechanisms can include, but are not limited to, mechanical latches, ties, clamps, or buttresses, or magnetic or magnetized surfaces. The ability to mechanically couple surgical robot 4 and camera tracking system 6 can allow for surgical system 2 to maneuver and move as a single unit, and allow surgical system 2 to have a small footprint in an area, allow easier movement through narrow passages and around turns, and allow storage within a smaller area.

An orthopedic surgical procedure may begin with the surgical system 2 moving from medical storage to a medical procedure room. The surgical system 2 may be maneuvered through doorways, halls, and elevators to reach a medical procedure room. Within the room, the surgical system 2 may be physically separated into two separate and distinct systems, the surgical robot 4 and the camera tracking system 6. Surgical robot 4 may be positioned adjacent the patient at any suitable location to properly assist medical personnel. Camera tracking system 6 may be positioned at the base of the patient, at patient shoulders or any other location suitable to track the present pose and movement of the pose of tracks portions of the surgical robot 4 and the patient. Surgical robot 4 and camera tracking system 6 may be powered by an onboard power source and/or plugged into an external wall outlet.

Surgical robot 4 may be used to assist a surgeon by holding and/or using tools during a medical procedure. To properly utilize and hold tools, surgical robot 4 may rely on a plurality of motors, computers, and/or actuators to function properly. Illustrated in FIG. 1, robot body 8 may act as the structure in which the plurality of motors, computers, and/or actuators may be secured within surgical robot 4. Robot body 8 may also provide support for robot telescoping support arm 16. In some embodiments, robot body 8 may be made of any suitable material. Suitable material may be, but is not limited to, metal such as titanium, aluminum, or stainless steel, carbon fiber, fiberglass, or heavy-duty plastic. The size of robot body 8 may provide a solid platform supporting attached components, and may house, conceal, and protect the plurality of motors, computers, and/or actuators that may operate attached components.

Robot base 10 may act as a lower support for surgical robot 4. In some embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may be made of any suitable material. Suitable material may be, but is not limited to, metal such as titanium, aluminum, or stainless steel, carbon fiber, fiberglass, or heavy-duty plastic or resin. Robot base 10 may cover, protect, and support powered wheels 12.

In some embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for surgical system 2 to maneuver into any location and stabilize and/or level surgical system 2. A rod, located within or adjacent to powered wheel 12, may be pressed into a surface by the motor. The rod, not pictured, may be made of any suitable metal to lift surgical system 2. Suitable metal may be, but is not limited to, stainless steel, aluminum, or titanium. Additionally, the rod may comprise at the contact-surface-side end a buffer, not pictured, which may prevent the rod from slipping and/or create a suitable contact surface. The material may be any suitable material to act as a buffer. Suitable material may be, but is not limited to, a plastic, neoprene, rubber, or textured metal. The rod may lift powered wheel 10, which may lift surgical system 2, to any height required to level or otherwise fix the orientation of the surgical system 2 in relation to a patient. The weight of surgical system 2, supported through small contact areas by the rod on each wheel, prevents surgical system 2 from moving during a medical procedure. This rigid positioning may prevent objects and/or people from moving surgical system 2 by accident.

Moving surgical system 2 may be facilitated using robot railing 14. Robot railing 14 provides a person with the ability to move surgical system 2 without grasping robot body 8. As illustrated in FIG. 1, robot railing 14 may run the length of robot body 8, shorter than robot body 8, and/or may run longer the length of robot body 8. Robot railing 14 may be made of any suitable material. Suitable material may be, but is not limited to, metal such as titanium, aluminum, or stainless steel, carbon fiber, fiberglass, or heavy-duty plastic. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the surgical system 2 due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In some embodiments, robot telescoping support 16 may extend and contract in a vertical direction. Robot telescoping support 16 may be made of any suitable material. Suitable material may be, but is not limited to, metal such as titanium or stainless steel, carbon fiber, fiberglass, or heavy-duty plastic. The body of robot telescoping support 16 may be any width and/or height in which to support the stress and weight placed upon it.

In some embodiments, medical personnel may move SCARA 24 through a command submitted by the medical personnel. The command may originate from input received on display 34 and/or a tablet. The command may come from the depression of a switch and/or the depression of a plurality of switches. Best illustrated in FIGS. 4 and 5, an activation assembly 60 may include a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 easily. Additionally, when the SCARA 24 is not receiving a command to move, the SCARA 24 may lock in place to prevent accidental movement by personnel and/or other objects. By locking in place, the SCARA 24 provides a solid platform upon which a passive end effector 1100 and connected surgical saw 1140, shown in FIGS. 4 and 4, are ready for use in a medical operation.

Robot support arm 18 may be disposed on robot telescoping support 16 by various mechanisms. In some embodiments, best seen in FIGS. 1 and 2, robot support arm 18 rotates in any direction in regard to robot telescoping support 16. Robot support arm 18 may rotate three hundred and sixty degrees around robot telescoping support 16. Robot arm 20 may connect to robot support arm 18 at any suitable location. Robot arm 20 may attach to robot support arm 16 by various mechanisms. Suitable mechanisms may be, but is not limited to, nuts and bolts, ball and socket fitting, press fitting, weld, adhesion, screws, rivets, clamps, latches, and/or any combination thereof. Robot arm 20 may rotate in any direction in regards to robot support arm 18, in embodiments, robot arm 20 may rotate three hundred and sixty degrees in regards to robot support arm 18. This free rotation may allow an operator to position robot arm 20 as planned.

Figure 4:
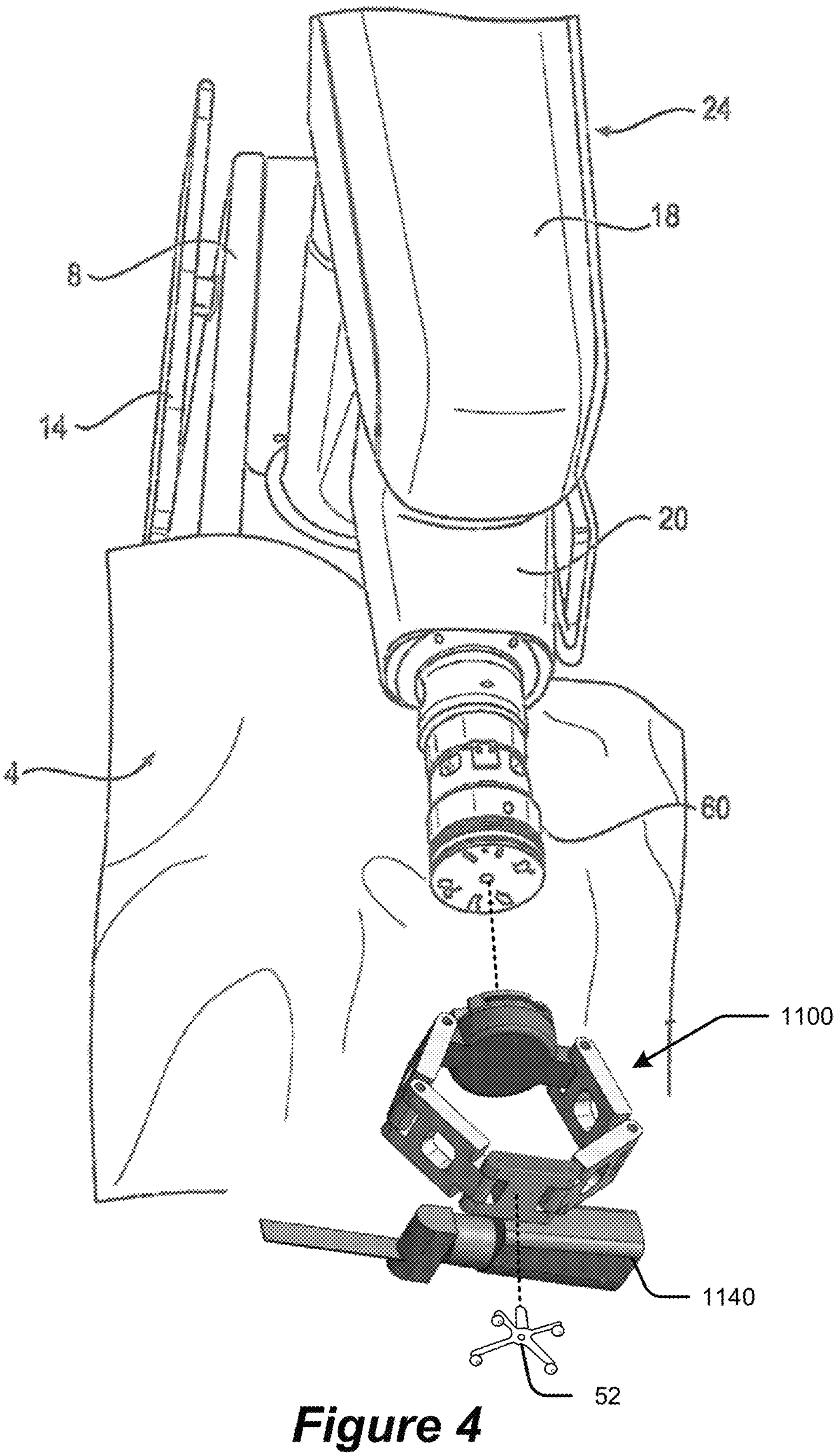
FIG. 4 illustrates an embodiment of a passive end effector that is connectable to a robot arm and configured according to some embodiments of the present disclosure.
Figure 5:
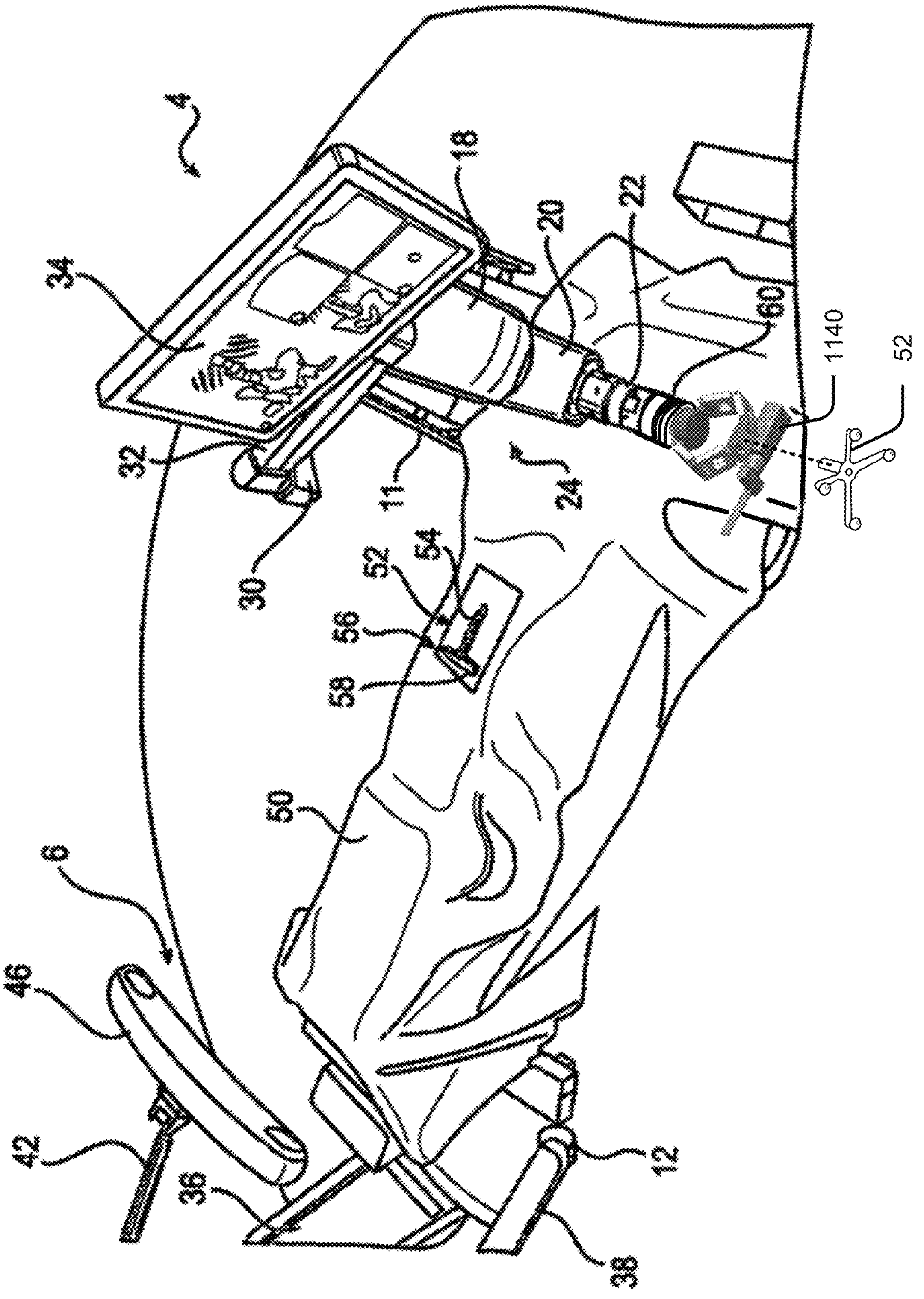
FIG. 5 illustrates a medical operation in which a surgical robot and a camera system are disposed around a patient.

The passive end effector 1100 in FIGS. 4 and 5 may attach to robot arm 20 in any suitable location. As will be explained in further detail below, the passive end effector 1100 includes a base, a first mechanism, and a second mechanism. The base is configured to attach to an end effector coupler 22 of the robot arm 20 positioned by the surgical robot 4. Various mechanisms by which the base can attach to the end effector coupler 22 can include, but are not limited to, latch, clamp, nuts and bolts, ball and socket fitting, press fitting, weld, adhesion, screws, rivets, and/or any combination thereof. The first mechanism extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections, and may be configured to constrain movement of the tool attachment mechanism to a range of movement within a working plane. The rotatable connections may be pivot joints allowing 1 degree-of-freedom (DOF) motion, universal joints allowing 2 DOF motions, or ball joints allowing 3 DOF motions. The tool attachment mechanism is configured to connect to a surgical saw 1140 having a saw blade. The surgical saw 1140 may be configured to oscillate the saw blade for cutting. The first and second mechanisms may be configured to constrain a cutting plane of the saw blade to be parallel to the working plane. Pivot joints may be preferably used for connecting the planar mechanisms when the passive end effector is to be configured to constrain motion of the saw blade to the cutting plane.

The tool attachment mechanism may connect to the surgical saw 1140 through various mechanisms that can include, but are not limited to, a screw, nut and bolt, clamp, latch, tie, press fit, or magnet. In some embodiments, a dynamic reference array 52 is attached to the passive end effector 1100, e.g., to the tool attachment mechanism, and/or is attached to the surgical saw 1140. Dynamic reference arrays, also referred to as "DRAs" herein, are rigid bodies which may be disposed on a patient, the surgical robot, the passive end effector, and/or the surgical saw in a navigated surgical procedure. The camera tracking system 6 or other 3D localization system is configured to track in real-time the pose (e.g., positions and rotational orientations) of tracking markers of the DRA. The tracking markers include fiducials, such as the illustrated arrangement of balls. This tracking of 3D coordinates of tracking markers can allow the surgical system 2 to determine the pose of the DRA 52 in any space in relation to the target anatomical structure of the patient 50 in FIG. 5.

As illustrated in FIG. 1, a light indicator 28 may be positioned on top of the SCARA 24. Light indicator 28 may illuminate as any type of light to indicate "conditions" in which surgical system 2 is currently operating. For example, the illumination of green may indicate that all systems are normal. Illuminating red may indicate that surgical system 2 is not operating normally. A pulsating light may mean surgical system 2 is performing a function. Combinations of light and pulsation may create a nearly limitless amount of combinations in which to communicate the current operating conditions, states, or other operational indications. In some embodiments, the light may be produced by LED bulbs, which may form a ring around light indicator 28. Light indicator 28 may comprise a fully permeable material that may let light shine through the entirety of light indicator 28.

Figure 2:
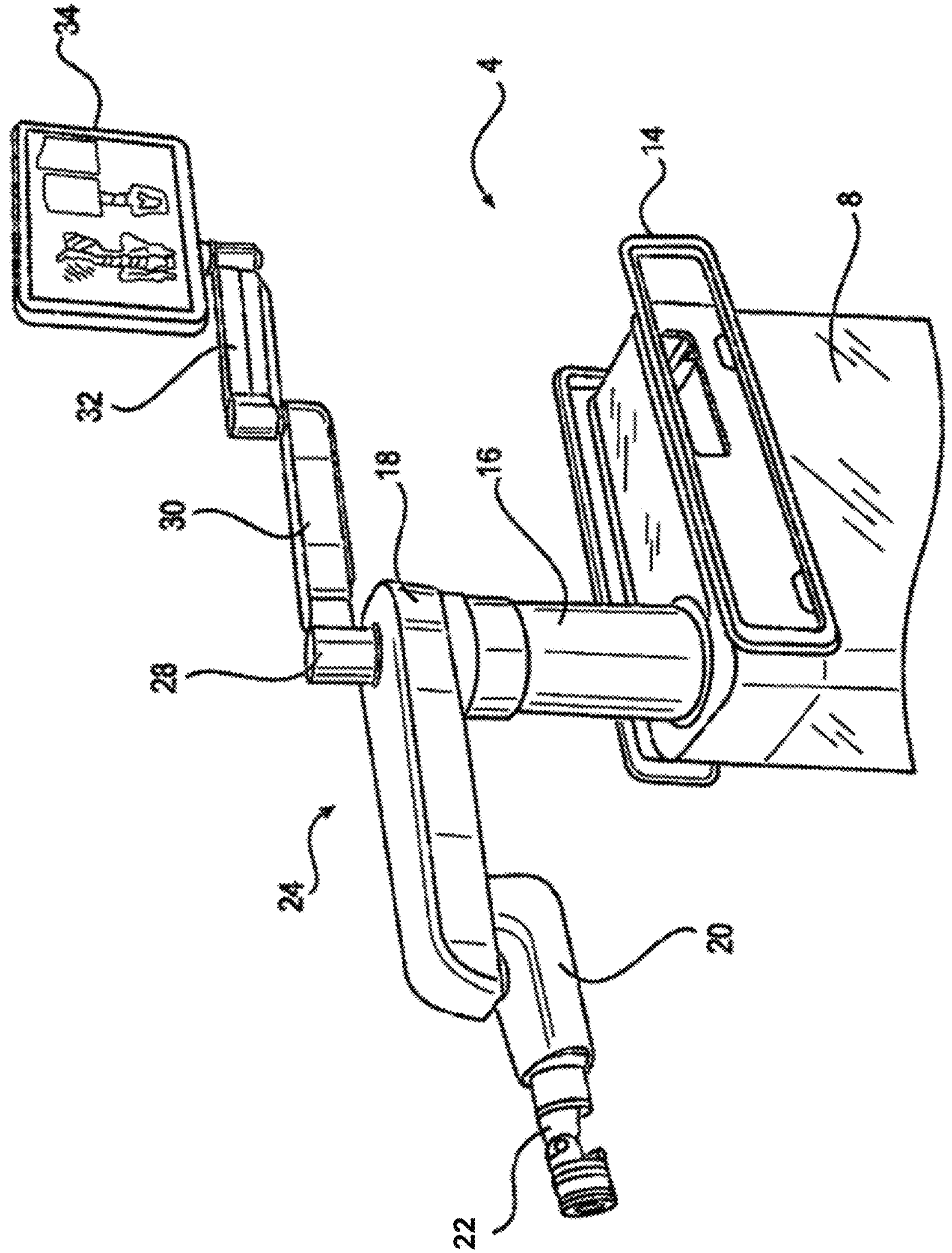
FIG. 2 illustrates a surgical robot component of the surgical system of FIG. 1 according to some embodiments of the present disclosure.

Light indicator 28 may be attached to lower display support 30. Lower display support 30, as illustrated in FIG. 2 may allow an operator to maneuver display 34 to any suitable location. Lower display support 30 may attach to light indicator 28 by any suitable mechanism. In embodiments, lower display support 30 may rotate about light indicator 28. In embodiments, lower display support 30 may attach rigidly to light indicator 28. Light indicator 28 may then rotate three hundred and sixty degrees about robot support arm 18. Lower display support 30 may be of any suitable length, a suitable length may be about eight inches to about thirty four inches. Lower display support 30 may act as a base for upper display support 32.

Upper display support 32 may attach to lower display support 30 by any suitable mechanism. Upper display support 32 may be of any suitable length, a suitable length may be about eight inches to about thirty four inches. In embodiments, as illustrated in FIG. 1, upper display support 32 may allow display 34 to rotate three hundred and sixty degrees in relation to upper display support 32. Likewise, upper display support 32 may rotate three hundred and sixty degrees in relation to lower display support 30.

Display 34 may be any device which may be supported by upper display support 32. In embodiments, as illustrated in FIG. 2, display 34 may produce color and/or black and white images. The width of display 34 may be about eight inches to about thirty inches wide. The height of display 34 may be about six inches to about twenty two inches tall. The depth of display 34 may be about one-half inch to about four inches.

In embodiments, a tablet may be used in conjunction with display 34 and/or without display 34. In embodiments, the table may be disposed on upper display support 32, in place of display 34, and may be removable from upper display support 32 during a medical operation. In addition the tablet may communicate with display 34. The tablet may be able to connect to surgical robot 4 by any suitable wireless and/or wired connection. In some embodiments, the tablet may be able to program and/or control surgical system 2 during a medical operation. When controlling surgical system 2 with the tablet, all input and output commands may be duplicated on display 34. The use of a tablet may allow an operator to manipulate surgical robot 4 without having to move around patient 50 and/or to surgical robot 4.

As illustrated in FIG. 5, camera tracking system 6 works in conjunction with surgical robot 4 through wired or wireless communication networks. Referring to FIGS. 1 and 5, camera tracking system 6 can include some similar components to the surgical robot 4. For example, camera body 36 may provide the functionality found in robot body 8. Robot body 8 may provide the structure upon which camera 46 is mounted. The structure within robot body 8 may also provide support for the electronics, communication devices, and power supplies used to operate camera tracking system 6. Camera body 36 may be made of the same material as robot body 8. Camera tracking system 6 may communicate directly to the tablet and/or display 34 by a wireless and/or wired network to enable the tablet and/or display 34 to control the functions of camera tracking system 6.

Camera body 36 is supported by camera base 38. Camera base 38 may function as robot base 10. In the embodiment of FIG. 1, camera base 38 may be wider than robot base 10.

The width of camera base 38 may allow for camera tracking system 6 to connect with surgical robot 4. As illustrated in FIG. 1, the width of camera base 38 may be large enough to fit outside robot base 10. When camera tracking system 6 and surgical robot 4 are connected, the additional width of camera base 38 may allow surgical system 2 additional maneuverability and support for surgical system 2.

As with robot base 10, a plurality of powered wheels 12 may attach to camera base 38. Powered wheel 12 may allow camera tracking system 6 to stabilize and level or set fixed orientation in regards to patient 50, similar to the operation of robot base 10 and powered wheels 12. This stabilization may prevent camera tracking system 6 from moving during a medical procedure and may keep camera 46 from losing track of one or more DRAs 52 connected to an anatomical structure 54 and/or tool 58 within a designated area 56 as shown in FIG. 5. This stability and maintenance of tracking enhances the ability of surgical robot 4 to operate effectively with camera tracking system 6. Additionally, the wide camera base 38 may provide additional support to camera tracking system 6. Specifically, a wide camera base 38 may prevent camera tracking system 6 from tipping over when camera 46 is disposed over a patient, as illustrated in FIG. 5. Without the wide camera base 38, the outstretched camera 46 may unbalance camera tracking system 6, which may result in camera tracking system 6 falling over.

Camera telescoping support 40 may support camera 46. In embodiments, telescoping support 40 may move camera 46 higher or lower in the vertical direction. Telescoping support 40 may be made of any suitable material in which to support camera 46. Suitable material may be, but is not limited to, metal such as titanium, aluminum, or stainless steel, carbon fiber, fiberglass, or heavy-duty plastic. Camera handle 48 may be attached to camera telescoping support 40 at any suitable location. Cameral handle 48 may be any suitable handle configuration. A suitable configuration may be, but is not limited to, a bar, circular, triangular, square, and/or any combination thereof. As illustrated in FIG. 1, camera handle 48 may be triangular, allowing an operator to move camera tracking system 6 into a planned position before a medical operation. In embodiments, camera handle 48 may be used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position camera 46 in any suitable location. Lower camera support arm 42 may be made of any suitable material in which to support camera 46. Suitable material may be, but is not limited to, metal such as titanium, aluminum, or stainless steel, carbon fiber, fiberglass, or heavy-duty plastic. Cross-section of lower camera support arm 42 may be any suitable shape. Suitable cross-sectional shape may be, but is not limited to, circle, square, rectangle, hexagon, octagon, or i-beam. The cross-sectional length and width may be about one to ten inches. Length of the lower camera support arm may be about four inches to about thirty-six inches. Lower camera support arm 42 may connect to telescoping support 40 by any suitable mechanism. Suitable mechanism may be, but is not limited to, nuts and bolts, ball and socket fitting, press fitting, weld, adhesion, screws, rivets, clamps, latches, and/or any combination thereof. Lower camera support arm 42 may be used to provide support for camera 46. Camera 46 may be attached to lower camera support arm 42 by any suitable mechanism. Suitable mechanism may be, but is not limited to, nuts and bolts, ball and socket fitting, press fitting, weld, adhesion, screws, rivets, and/or any combination thereof. Camera 46 may pivot in any direction at the attachment area between camera 46 and lower camera support arm 42. In embodiments a curved rail 44 may be disposed on lower camera support arm 42.

Figure 3:
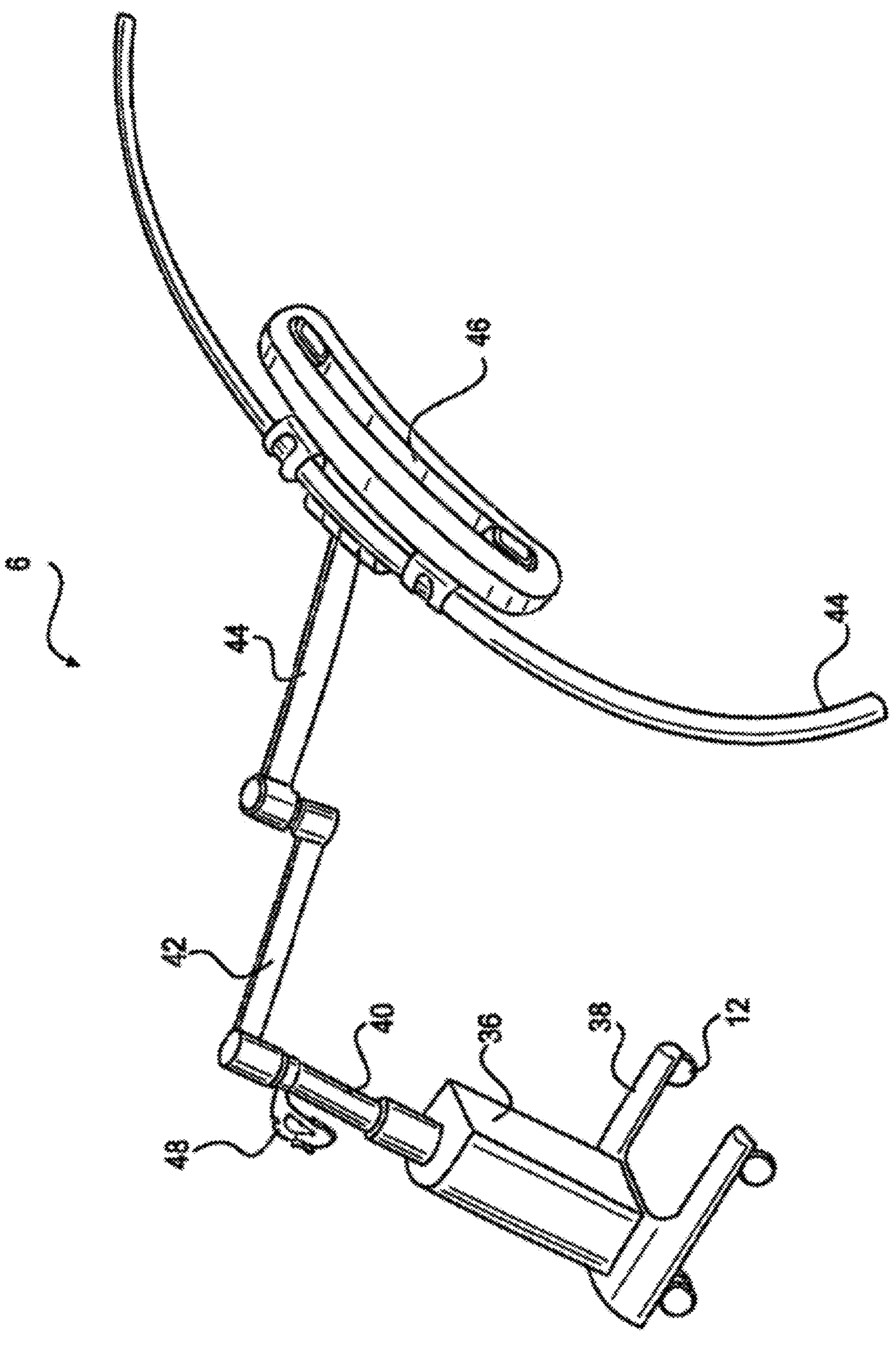
FIG. 3 illustrates a camera tracking system component of the surgical system of FIG. 1 according to some embodiments of the present disclosure.

Curved rail 44 may be disposed at any suitable location on lower camera support arm 42. As illustrated in FIG. 3, curved rail 44 may attach to lower camera support arm 42 by any suitable mechanism. Suitable mechanism may be, but are not limited to nuts and bolts, ball and socket fitting, press fitting, weld, adhesion, screws, rivets, clamps, latches, and/or any combination thereof. Curved rail 44 may be of any suitable shape, a suitable shape may be a crescent, circular, oval, elliptical, and/or any combination thereof. In embodiments, curved rail 44 may be any appropriate length. An appropriate length may be about one foot to about six feet. Camera 46 may be moveably disposed along curved rail 44. Camera 46 may attach to curved rail 44 by any suitable mechanism. Suitable mechanism may be, but are not limited to rollers, brackets, braces, motors, and/or any combination thereof. Motors and rollers, not illustrated, may be used to move camera 46 along curved rail 44. As illustrated in FIG. 3, during a medical procedure, if an object prevents camera 46 from viewing one or more DRAs 52, the motors may move camera 46 along curved rail 44 using rollers. This motorized movement may allow camera 46 to move to a new position that is no longer obstructed by the object without moving camera tracking system 6. While camera 46 is obstructed from viewing DRAs 52, camera tracking system 6 may send a stop signal to surgical robot 4, display 34, and/or a tablet. The stop signal may prevent SCARA 24 from moving until camera 46 has reacquired DRAs 52. This stoppage may prevent SCARA 24 and/or end effector coupler 22 from moving and/or using medical tools without being tracked by surgical system 2.

Figure 6:
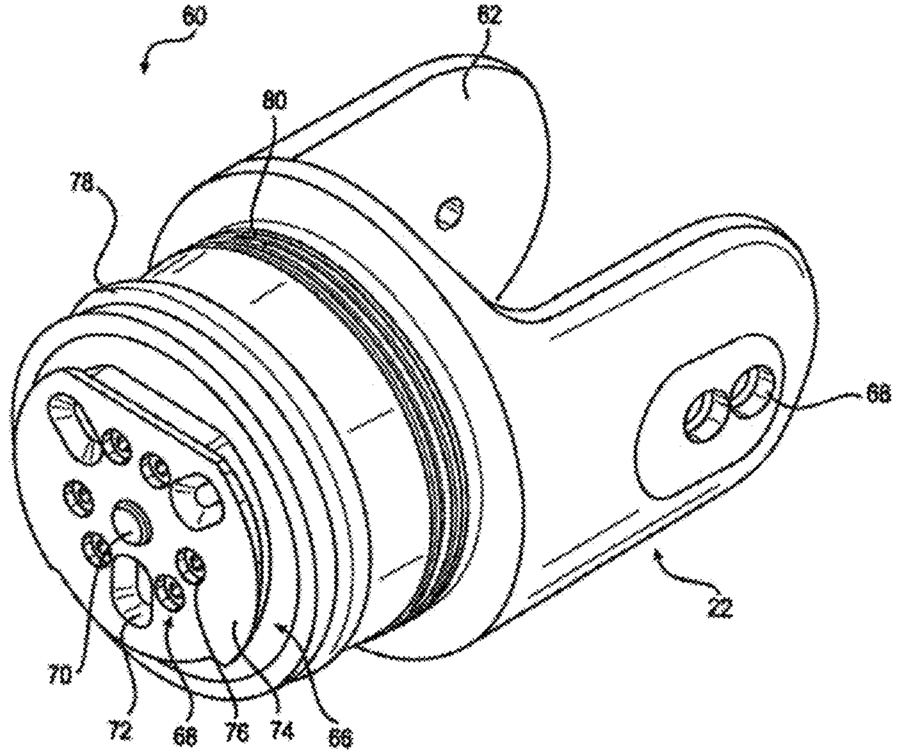
FIG. 6 illustrates an embodiment of an end effector coupler of a robot arm configured for connection to a passive end effector according to some embodiments of the present disclosure.

End effector coupler 22, as illustrated in FIG. 6, is configured to connect various types of passive end effectors to surgical robot 4. End effector coupler 22 can include a saddle joint 62, an activation assembly 60, a load cell 64 (FIG. 7), and a connector 66. Saddle joint 62 may attach end effector coupler 22 to SCARA 24. Saddle joint 62 may be made of any suitable material. Suitable material may be, but is not limited to metal such as titanium, aluminum, or stainless steel, carbon fiber, fiberglass, or heavy-duty plastic. Saddle joint 62 may be made of a single piece of metal which may provide end effector with additional strength and durability. The saddle joint 62 may attach to SCARA 24 by an attachment point 68. There may be a plurality of attachment points 68 disposed about saddle joint 62. Attachment points 68 may be sunk, flush, and/or disposed upon saddle joint 62. In some examples, screws, nuts and bolts, and/or any combination thereof may pass through attachment point 68 and secure saddle joint 62 to SCARA 24. The nuts and bolts may connect saddle joint 62 to a motor, not illustrated, within SCARA 24. The motor may move saddle joint 62 in any direction. The motor may further prevent saddle joint 62 from moving from accidental bumps and/or accidental touches by actively servoing at the current location or passively by applying spring actuated brakes.

Figure 7:
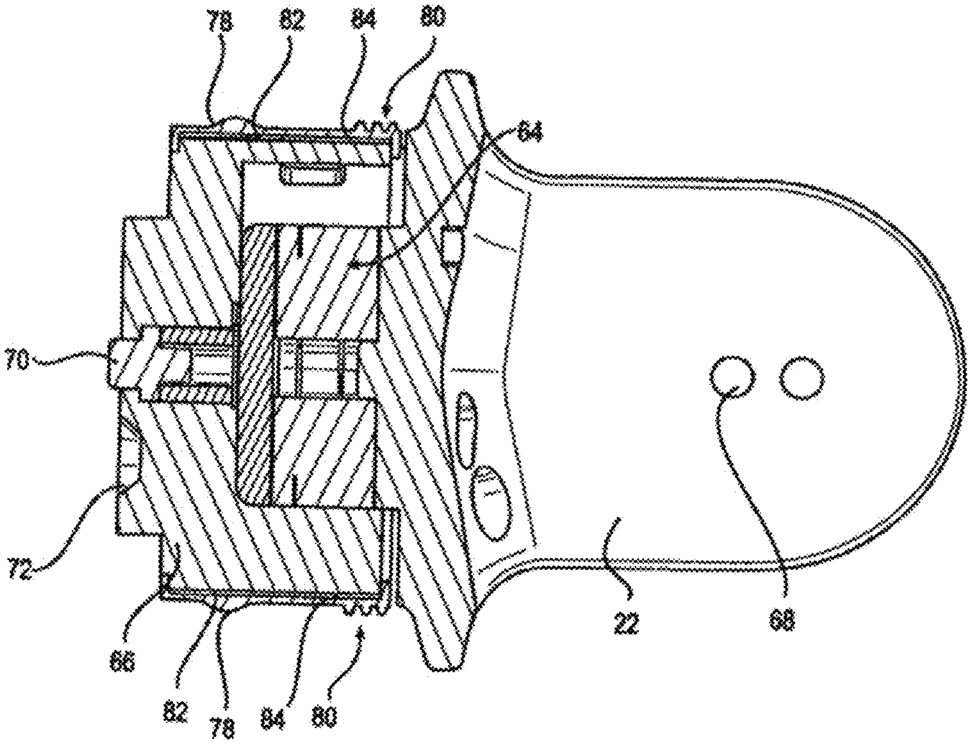
FIG. 7 illustrates an embodiment of a cut away of the end effector coupler of FIG. 6.

The end effector coupler 22 can include a load cell 64 interposed between the saddle join 62 and a connected passive end effector. Load cell 64, as illustrated in FIG. 7 may attach to saddle joint 62 by any suitable mechanism.

Suitable mechanism may be, but is not limited to, screws, nuts and bolts, threading, press fitting, and/or any combination thereof.

Figure 8:
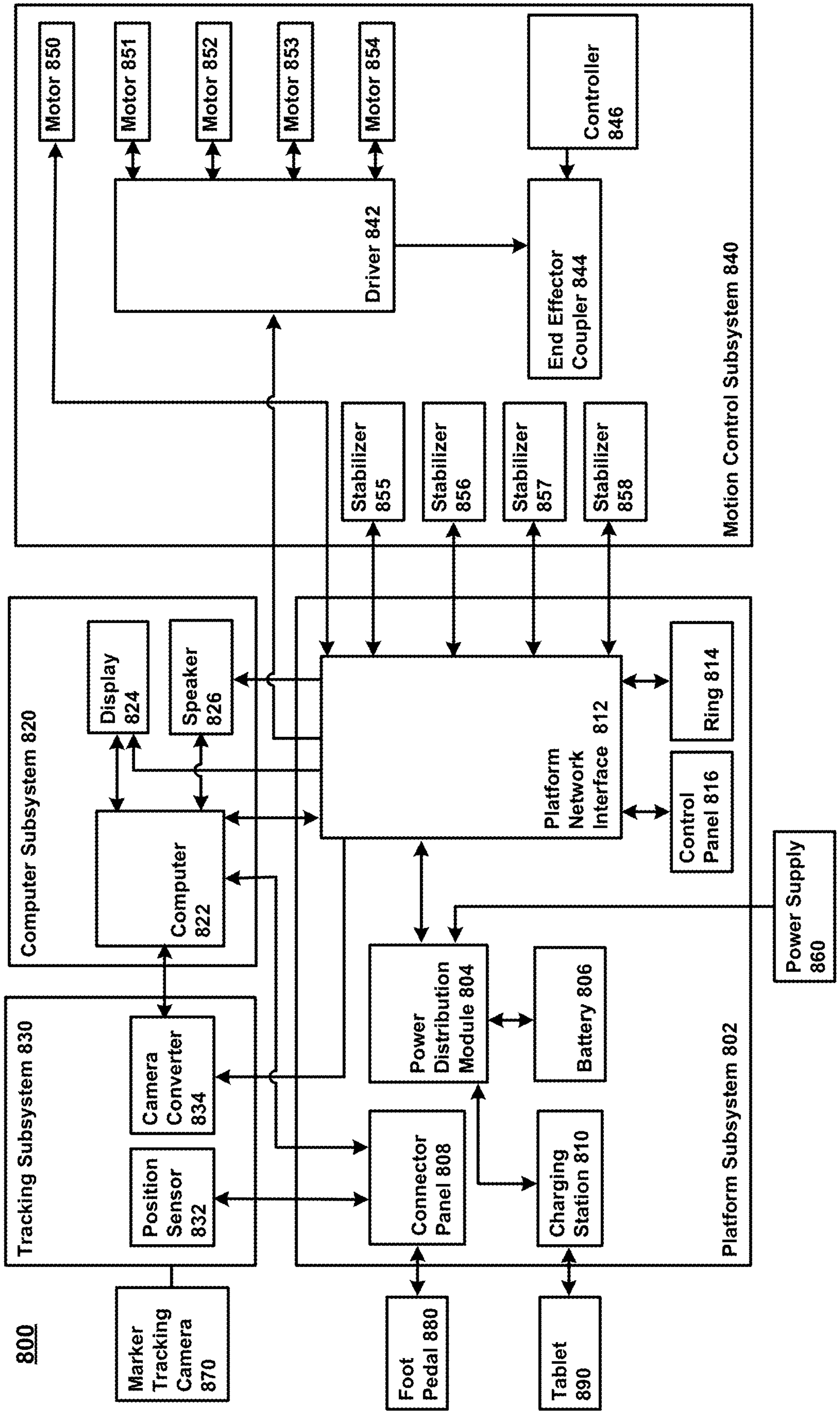
FIG. 8 illustrates a block diagram of components of a surgical system according to some embodiments of the present disclosure.

FIG. 8 illustrates a block diagram of components of a surgical system 800 according to some embodiments of the present disclosure. Referring to FIGS. 7 and 8, load cell 64 may be any suitable instrument used to detect and measure forces. In some examples, load cell 64 may be a six axis load cell, a three-axis load cell or a uniaxial load cell. Load cell 64 may be used to track the force applied to end effector coupler 22. In some embodiments the load cell 64 may communicate with a plurality of motors 850, 851, 852, 853, and/or 854. As load cell 64 senses force, information as to the amount of force applied may be distributed from a switch array and/or a plurality of switch arrays to a controller 846. Controller 846 may take the force information from load cell 64 and process it with a switch algorithm. The switch algorithm is used by the controller 846 to control a motor driver 842. The motor driver 842 controls operation of one or more of the motors. Motor driver 842 may direct a specific motor to produce, for example, an equal amount of force measured by load cell 64 through the motor. In some embodiments, the force produced may come from a plurality of motors, e.g., 850-854, as directed by controller 846. Additionally, motor driver 842 may receive input from controller 846. Controller 846 may receive information from load cell 64 as to the direction of force sensed by load cell 64. Controller 846 may process this information using a motion controller algorithm. The algorithm may be used to provide information to specific motor drivers 842. To replicate the direction of force, controller 846 may activate and/or deactivate certain motor drivers 842. Controller 846 may control one or more motors, e.g. one or more of 850-854, to induce motion of passive end effector 1100 in the direction of force sensed by load cell 64. This force-controlled motion may allow an operator to move SCARA 24 and passive end effector 1100 effortlessly and/or with very little resistance. Movement of passive end effector 1100 can be performed to position passive end effector 1100 in any suitable pose (i.e., location and angular orientation relative to defined three-dimensional (3D) orthogonal reference axes) for use by medical personnel.

Connector 66 is configured to be connectable to the base of the passive end effector 1100 and is connected to load cell 64. Connector 66 can include attachment points 68, a sensory button 70, tool guides 72, and/or tool connections 74. Best illustrated in FIGS. 6 and 8, there may be a plurality of attachment points 68. Attachment points 68 may connect connector 66 to load cell 64. Attachment points 68 may be sunk, flush, and/or disposed upon connector 66. Attachment points 68 and 76 can be used to attach connector 66 to load cell 64 and/or to passive end effector 1100. In some examples, Attachment points 68 and 76 may include screws, nuts and bolts, press fittings, magnetic attachments, and/or any combination thereof.

As illustrated in FIG. 6, a sensory button 70 may be disposed about center of connector 66. Sensory button 70 may be depressed when a passive end effector 1100 is connected to SCARA 24. Depression of sensory button 70 may alert surgical robot 4, and in turn medical personnel, that a passive end effector 1100 has been attached to SCARA 24. As illustrated in FIG. 6, guides 72 may be used to facilitate proper attachment of passive end effector 1100 to SCARA 24. Guides 72 may be sunk, flush, and/or disposed upon connector 66. In some examples there may be a plurality of guides 72 and may have any suitable patterns and may be oriented in any suitable direction. Guides 72 may be any suitable shape to facilitate attachment of passive end effector 1100 to SCARA 24. A suitable shape may be, but is not limited to, circular, oval, square, polyhedral, and/or any combination thereof. Additionally, guides 72 may be cut with a bevel, straight, and/or any combination thereof.

Connector 66 may have attachment points 74. As illustrated in FIG. 6, attachment points 74 may form a ledge and/or a plurality of ledges. Attachment points 74 may provide connector 66 a surface upon which passive end effector 1100 may clamp. In some embodiments, attachment points 74 are disposed about any surface of connector 66 and oriented in any suitable manner in relation to connector 66.

Activation assembly 60, best illustrated in FIGS. 6 and 7, may encircle connector 66. In some embodiments, activation assembly 60 may take the form of a bracelet that wraps around connector 66. In some embodiments, activation assembly 60, may be located in any suitable area within surgical system 2. In some examples, activation assembly 60 may be located on any part of SCARA 24, any part of end effector coupler 22, may be worn by medical personnel (and communicate wirelessly), and/or any combination thereof. Activation assembly 60 may be made of any suitable material. Suitable material may be, but is not limited to neoprene, plastic, rubber, gel, carbon fiber, fabric, and/or any combination thereof. Activation assembly 60 may comprise of a primary button 78 and a secondary button 80.

Primary button 78 and secondary button 80 may encircle the entirety of connector 66. Primary button 78 may be a single ridge, as illustrated in FIG. 6, which may encircle connector 66. In some examples, primary button 78 may be disposed upon activation assembly 60 along the end farthest away from saddle joint 62. Primary button 78 may be disposed upon primary activation switch 82, best illustrated on FIG. 7. Primary activation switch 82 may be disposed between connector 66 and activation assembly 60. In some examples, there may be a plurality of primary activation switches 82, which may be disposed adjacent and beneath primary button 78 along the entire length of primary button 78. Depressing primary button 78 upon primary activation switch 82 may allow an operator to move SCARA 24 and end effector coupler 22. As discussed above, once set in place, SCARA 24 and end effector coupler 22 may not move until an operator programs surgical robot 4 to move SCARA 24 and end effector coupler 22, or is moved using primary button 78 and primary activation switch 82. In some examples, it may require the depression of at least two non-adjacent primary activation switches 82 before SCARA 24 and end effector coupler 22 will respond to operator commands. Depression of at least two primary activation switches 82 may prevent the accidental movement of SCARA 24 and end effector coupler 22 during a medical procedure.

Activated by primary button 78 and primary activation switch 82, load cell 64 may measure the force magnitude and/or direction exerted upon end effector coupler 22 by an operator, i.e. medical personnel. This information may be transferred to motors within SCARA 24 that may be used to move SCARA 24 and end effector coupler 22. Information as to the magnitude and direction of force measured by load cell 64 may cause the motors to move SCARA 24 and end effector coupler 22 in the same direction as sensed by load cell 64. This force-controlled movement may allow the operator to move SCARA 24 and end effector coupler 22 easily and without large amounts of exertion due to the motors moving SCARA 24 and end effector coupler 22 at the same time the operator is moving SCARA 24 and end effector coupler 22.

Secondary button 80, as illustrated in FIG. 6, may be disposed upon the end of activation assembly 60 closest to saddle joint 62. In some examples secondary button 80 may comprise a plurality of ridges. The plurality of ridges may be disposed adjacent to each other and may encircle connector 66. Additionally, secondary button 80 may be disposed upon secondary activation switch 84. Secondary activation switch 84, as illustrated in FIG. 7, may be disposed between secondary button 80 and connector 66. In some examples, secondary button 80 may be used by an operator as a "selection" device. During a medical operation, surgical robot 4 may notify medical personnel to certain conditions by display 34 and/or light indicator 28. Medical personnel may be prompted by surgical robot 4 to select a function, mode, and/or assess the condition of surgical system 2. Depressing secondary button 80 upon secondary activation switch 84 a single time may activate certain functions, modes, and/or acknowledge information communicated to medical personnel through display 34 and/or light indicator 28. Additionally, depressing secondary button 80 upon secondary activation switch 84 multiple times in rapid succession may activate additional functions, modes, and/or select information communicated to medical personnel through display 34 and/or light indicator 28. In some examples, at least two non-adjacent secondary activation switches 84 may be depressed before secondary button 80 may function properly. This requirement may prevent unintended use of secondary button 80 from accidental bumping by medical personnel upon activation assembly 60. Primary button 78 and secondary button 80 may use software architecture 86 to communicate commands of medical personnel to surgical system 2.

FIG. 8 illustrates a block diagram of components of a surgical system 800 configured according to some embodiments of the present disclosure, and which may correspond to the surgical system 2 above. Surgical system 800 includes platform subsystem 802, computer subsystem 820, motion control subsystem 840, and tracking subsystem 830. Platform subsystem 802 includes battery 806, power distribution module 804, connector panel 808, and charging station 810. Computer subsystem 820 includes computer 822, display 824, and speaker 826. Motion control subsystem 840 includes driver circuit 842, motors 850, 851, 852, 853, 854, stabilizers 855, 856, 857, 858, end effector connector 844, and controller 846. Tracking subsystem 830 includes position sensor 832 and camera converter 834. Surgical system 800 may also include a removable foot pedal 880 and removable tablet computer 890.

Input power is supplied to surgical system 800 via a power source which may be provided to power distribution module 804. Power distribution module 804 receives input power and is configured to generate different power supply voltages that are provided to other modules, components, and subsystems of surgical system 800. Power distribution module 804 may be configured to provide different voltage supplies to connector panel 808, which may be provided to other components such as computer 822, display 824, speaker 826, driver 842 to, for example, power motors 850-854 and end effector coupler 844, and provided to camera converter 834 and other components for surgical system 800. Power distribution module 804 may also be connected to battery 806, which serves as temporary power source in the event that power distribution module 804 does not receive power from an input power. At other times, power distribution module 804 may serve to charge battery 806.

Connector panel 808 may serve to connect different devices and components to surgical system 800 and/or associated components and modules. Connector panel 808 may contain one or more ports that receive lines or connections from different components. For example, connector panel 808 may have a ground terminal port that may ground surgical system 800 to other equipment, a port to connect foot pedal 880, a port to connect to tracking subsystem 830, which may include position sensor 832, camera converter 834, and marker tracking cameras 870. Connector panel 808 may also include other ports to allow USB, Ethernet, HDMI communications to other components, such as computer 822.

Control panel 816 may provide various buttons or indicators that control operation of surgical system 800 and/or provide information from surgical system 800 for observation by an operator. For example, control panel 816 may include buttons to power on or off surgical system 800, lift or lower vertical column 16, and lift or lower stabilizers 855-858 that may be designed to engage casters 12 to lock surgical system 800 from physically moving. Other buttons may stop surgical system 800 in the event of an emergency, which may remove all motor power and apply mechanical brakes to stop all motion from occurring. Control panel 816 may also have indicators notifying the operator of certain system conditions such as a line power indicator or status of charge for battery 806.

Computer 822 of computer subsystem 820 includes an operating system and software to operate assigned functions of surgical system 800. Computer 822 may receive and process information from other components (for example, tracking subsystem 830, platform subsystem 802, and/or motion control subsystem 840) in order to display information to the operator. Further, computer subsystem 820 may provide output through the speaker 826 for the operator. The speaker may be part of the surgical robot, part of a head-mounted display component, or within another component of the surgical system 2. The display 824 may correspond to the display 34 shown in FIGS. 1 and 2, or may be a head-mounted display which projects images onto a see-through display screen which forms an augmented reality (AR) image that is overlaid on real-world objects viewable through the see-through display screen.

Tracking subsystem 830 may include position sensor 832 and camera converter 834. Tracking subsystem 830 may correspond to the camera tracking system 6 of FIG. 3. The marker tracking cameras 870 operate with the position sensor 832 to determine the pose of DRAs 52. This tracking may be conducted in a manner consistent with the present disclosure including the use of infrared or visible light technology that tracks the location of active or passive elements of DRAs 52, such as LEDs or reflective markers, respectively. The location, orientation, and position of structures having these types of markers, such as DRAs 52, is provided to computer 822 and which may be shown to an operator on display 824. For example, as shown in FIGS. 4 and 5, a surgical saw 1240 having a DRA 52 or which is connected to an end effector coupler 22 having a DRA 52 tracked in this manner (which may be referred to as a navigational space) may be shown to an operator in relation to a three dimensional image of a patient's anatomical structure.

Motion control subsystem 840 may be configured to physically move vertical column 16, upper arm 18, lower arm 20, or rotate end effector coupler 22. The physical movement may be conducted through the use of one or more motors 850-854. For example, motor 850 may be configured to vertically lift or lower vertical column 16. Motor 851 may be configured to laterally move upper arm 18 around a point of engagement with vertical column 16 as shown in FIG. 2. Motor 852 may be configured to laterally move lower arm 20 around a point of engagement with upper arm 18 as shown in FIG. 2. Motors 853 and 854 may be configured to move end effector coupler 22 to provide translational movement and rotation along in about three-dimensional axes. The surgical planning computer 910 shown in FIG. 9 can provide control input to the controller 846 that guides movement of the end effector coupler 22 to position a passive end effector, which is connected thereto, with a planned pose (i.e., location and angular orientation relative to defined 3D orthogonal reference axes) relative to an anatomical structure that is to be cut during a surgical procedure. Motion control subsystem 840 may be configured to measure position of the passive end effector structure using integrated position sensors (e.g. encoders). In one of the embodiments, position sensors are directly connected to at least one joint of the passive end effector structure, but may also be positioned in another location in the structure and remotely measure the joint position by interconnection of a timing belt, a wire, or any other synchronous transmission interconnection.

Figure 9:
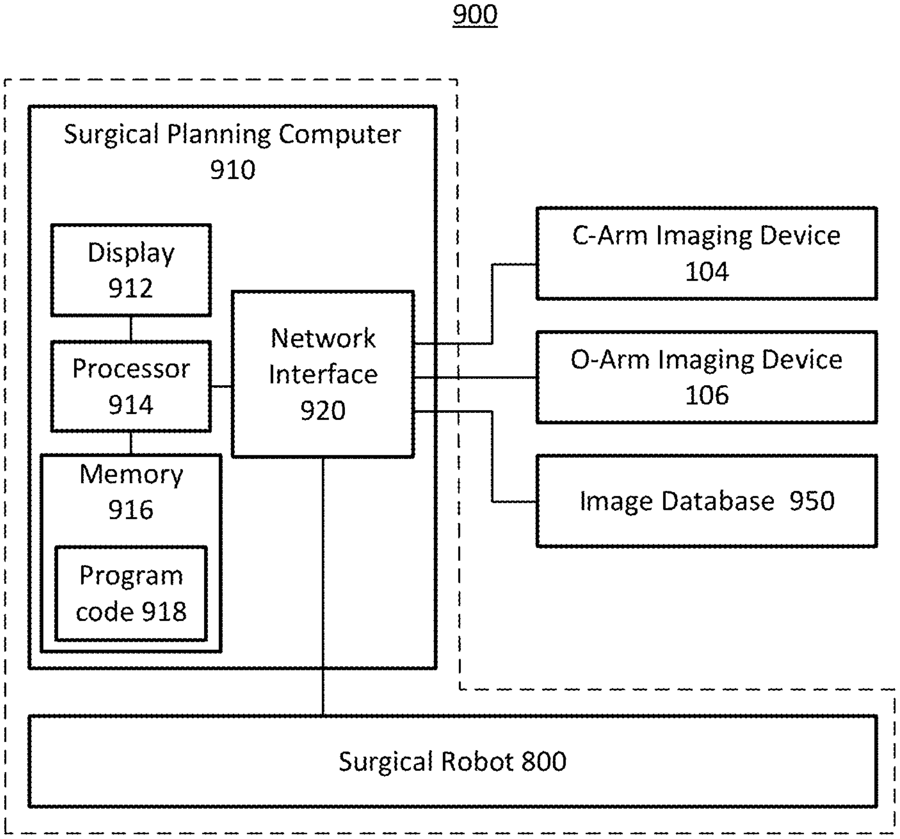
FIG. 9 illustrates a block diagram of a surgical system computer platform that includes a surgical planning computer which may be separate from and operationally connected to a surgical robot or at least partially incorporated therein according to some embodiments of the present disclosure.

FIG. 9 illustrates a block diagram of a surgical system computer platform 900 that includes a surgical planning computer 910 which may be separate from and operationally connected to a surgical robot 800 or at least partially incorporated therein according to some embodiments of the present disclosure. Alternatively, at least a portion of operations disclosed herein for the surgical planning computer 910 may be performed by components of the surgical robot 800 such as by the computer subsystem 820.

Referring to FIG. 9, the surgical planning computer 910 includes a display 912, at least one processor circuit 914 (also referred to as a processor for brevity), at least one memory circuit 916 (also referred to as a memory for brevity) containing computer readable program code 918, and at least one network interface 920 (also referred to as a network interface for brevity). The network interface 920 can be configured to connect to a C-Arm imaging device 104 in FIG. 10, an O-Arm imaging device 106 in FIG. 11, another medical imaging device, an image database 950 of medical images, components of the surgical robot 800, and/or other electronic equipment.

When the surgical planning computer 910 is at least partially integrated within the surgical robot 800, the display 912 may correspond to the display 34 of FIG. 2 and/or the tablet 890 of FIG. 8 and/or a head-mounted display, the network interface 920 may correspond to the platform network interface 812 of FIG. 8, and the processor 914 may correspond to the computer 822 of FIG. 8.

The processor 914 may include one or more data processing circuits, such as a general purpose and/or special purpose processor, e.g., microprocessor and/or digital signal processor. The processor 914 is configured to execute the computer readable program code 918 in the memory 916 to perform operations, which may include some or all of the operations described herein as being performed by a surgical planning computer.

The processor 914 can operate to display on the display device 912 an image of a bone that is received from one of the imaging devices 104 and 106 and/or from the image database 950 through the network interface 920. The processor 914 receives an operator's definition of where an anatomical structure, i.e. one or more bones, shown in one or more images is to be cut, such as by an operator touch selecting locations on the display 912 for planned surgical cuts or using a mouse-based cursor to define locations for planned surgical cuts.

The surgical planning computer 910 enables anatomy measurement, useful for knee surgery, like measurement of various angles determining center of hip, center of angles, natural landmarks (e.g. transepicondylar line, Whitesides line, posterior condylar line etc.), etc. Some measurements can be automatic while some others involve human input or assistance. This surgical planning computer 910 allows an operator to choose the correct implant for a patient, including choice of size and alignment. The surgical planning computer 910 enables automatic or semi-automatic (involving human input) segmentation (image processing) for CT images or other medical images. The surgical plan for a patient may be stored in a cloud-based server for retrieval by the surgical robot 800. During the surgery, the surgeon will choose which cut to make (e.g. posterior femur, proximal tibia etc.) using a computer screen (e.g. touchscreen) or augmented reality interaction via, e.g., a head-mounted display. The surgical robot 4 may automatically move the surgical saw to a planned position so that a target plane of planned cut is optimally placed within a workspace of the passive end effector interconnecting the surgical saw and the robot arm 20.

In some embodiments, the surgical system computer platform 900 can use two DRAs to tracking patient anatomy position: one on patient tibia and one on patient femur. The platform 900 may use standard navigated instruments for the registration and checks (e.g., a pointer similar to the one used in Globus ExcelsiusGPS system for spine surgery). Tracking markers allowing for detection of DRAs movement in reference to tracked anatomy can be used as well.

An important difficulty in knee surgery is how to plan the position of the implant in the knee and many surgeons struggle with to do it on a computer screen which is a 2D representation of 3D anatomy. The platform 900 could address this problem by using an augmented reality (AR) head-mounted display to generate an implant overlay around the actual patient knee. For example, the surgeon can be operationally displayed a virtual handle to grab and move the implant to a desired pose and adjust planned implant placement. Afterward, during surgery, the platform 900 could render the navigation through the AR head-mounted display to show surgeon what is not directly visible. Also, the progress of bone removal, e.g., depth or cut, can be displayed in real-time. Other features that may be displayed through AR can include, without limitation, gap or ligament balance along a range of joint motion, contact line on the implant along the range of joint motion, ligament tension and/or laxity through color or other graphical overlays, etc.

The surgical planning computer 910, in some embodiments, can allow planning for use of standard implants, e.g., posterior stabilized implants and cruciate retaining implants, cemented and cementless implants, revision systems for surgeries related to, for example, total or partial knee and/or hip replacement and/or trauma.

The processor 912 may graphically illustrate on the display 912 one or more cutting planes intersecting the displayed anatomical structure at the locations selected by the operator for cutting the anatomical structure. The processor 912 also determines one or more sets of angular orientations and locations where the end effector coupler 22 must be positioned so a cutting plane of the surgical saw will be aligned with a target plane to perform the operator defined cuts, and stores the sets of angular orientations and locations as data in a surgical plan data structure. The processor 912 uses the known range of movement of the tool attachment mechanism of the passive end effector to determine where the end effector coupler 22 attached to the robot arm 20 needs to be positioned.

The computer subsystem 820 of the surgical robot 800 receives data from the surgical plan data structure and receives information from the camera tracking system 6 indicating a present pose of an anatomical structure that is to be cut and indicating a present pose of the passive end effector and/or surgical saw tracked through DRAs. The computer subsystem 820 determines a pose of the target plane based on the surgical plan defining where the anatomical structure is to be cut and based on the pose of the anatomical structure. The computer subsystem 820 generates steering information based on comparison of the pose of the target plane and the pose of the surgical saw. The steering information indicates where the passive end effector needs to be moved so the cutting plane of the saw blade becomes aligned with the target plane and the saw blade becomes positioned a distance from the anatomical structure to be cut that is within the range of movement of the tool attachment mechanism of the passive end effector.

As explained above, a surgical robot includes a robot base, a robot arm connected to the robot base, and at least one motor operatively connected to move the robot arm relative to the robot base. The surgical robot also includes at least one controller, e.g. the computer subsystem 820 and the motion control subsystem 840, connected to the at least one motor and configured to perform operations.

As will be explained in further detail below with regard to FIGS. 12-19, a passive end effector includes a base configured to attach to an activation assembly of the robot arm, a first mechanism, and a second mechanism. The first mechanism extends between a rotatable connection to the base and a rotatable connection to a tool attachment mechanism. The second mechanism extends between a rotatable connection to the base and a rotatable connection to the tool attachment mechanism. The first and second mechanisms pivot about the rotatable connections which may be configured to constrain movement of the tool attachment mechanism to a range of movement within a working plane. The rotatable connections may be pivot joints allowing 1 degree-of-freedom (DOF) motion, universal joints allowing 2 DOF motions, or ball joints allowing 3 DOF motions. The tool attachment mechanism is configured to connect to the surgical saw comprising a saw blade for cutting. The first and second mechanisms may be configured to constrain a cutting plane of the saw blade to be parallel to the working plane.

In some embodiments, the operations performed by the at least one controller of the surgical robot also includes controlling movement of the at least one motor based on the steering information to reposition the passive end effector so the cutting plane of the saw blade becomes aligned with the target plane and the saw blade becomes positioned the distance from the anatomical structure to be cut that is within the range of movement of the tool attachment mechanism of the passive end effector. The steering information may be displayed to guide an operator's movement of the surgical saw and/or may be used by the at least one controller to automatically move the surgical saw.

In one embodiment, the operations performed by the at least one controller of the surgical robot also includes providing the steering information to a display device for display to guide operator movement of the passive end effector so the cutting plane of the saw blade becomes aligned with the target plane and so the saw blade becomes positioned the distance from the anatomical structure, which is to be cut, that is within the range of movement of the tool attachment mechanism of the passive end effector. The display device may correspond to the display 824 (FIG. 8), the display 34 of FIG. 1, and/or a head-mounted display.

For example, the steering information may be displayed on a head-mounted display which projects images onto a see-through display screen which forms an augmented reality image that is overlaid on real-world objects viewable through the see-through display screen. The operations may display a graphical representation of the target plane with a pose overlaid on a bone and with a relative orientation there between corresponding to the surgical plan for how the bone is planned to be cut. The operations may alternatively or additionally display a graphical representation of the cutting plane of the saw blade so that an operator may more easily align the cutting plane with the planned target plane for cutting the bone. The operator may thereby visually observe and perform movements to align the cutting plane of the saw blade with the target plane so the saw blade becomes positioned at the planned pose relative to the bone and within a range of movement of the tool attachment mechanism of the passive end effector.

Figure 10:
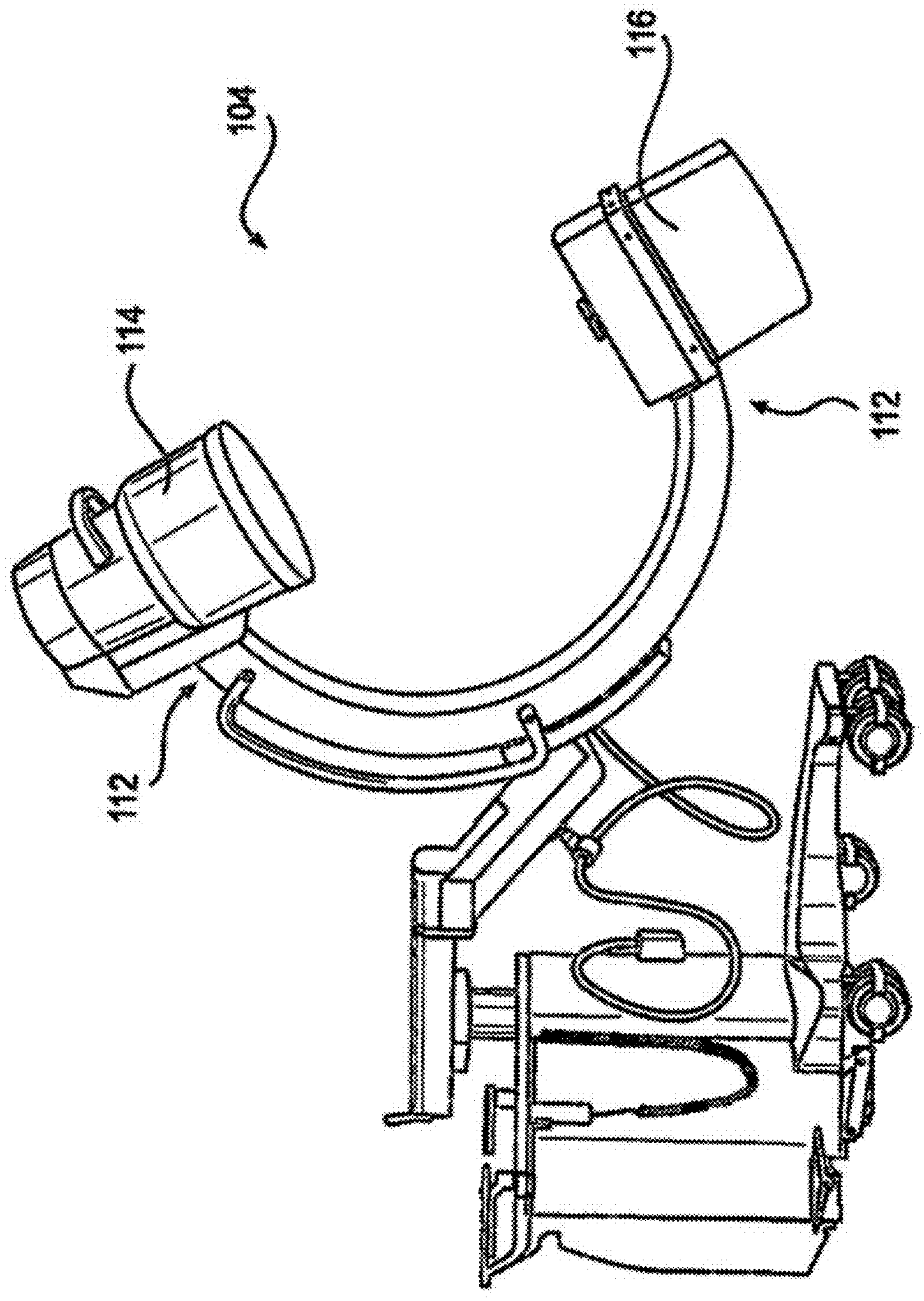
FIG. 10 illustrates an embodiment of a C-Arm imaging device that can be used in combination with the surgical robot and passive end effector in accordance with some embodiments of the present disclosure.
Figure 11:
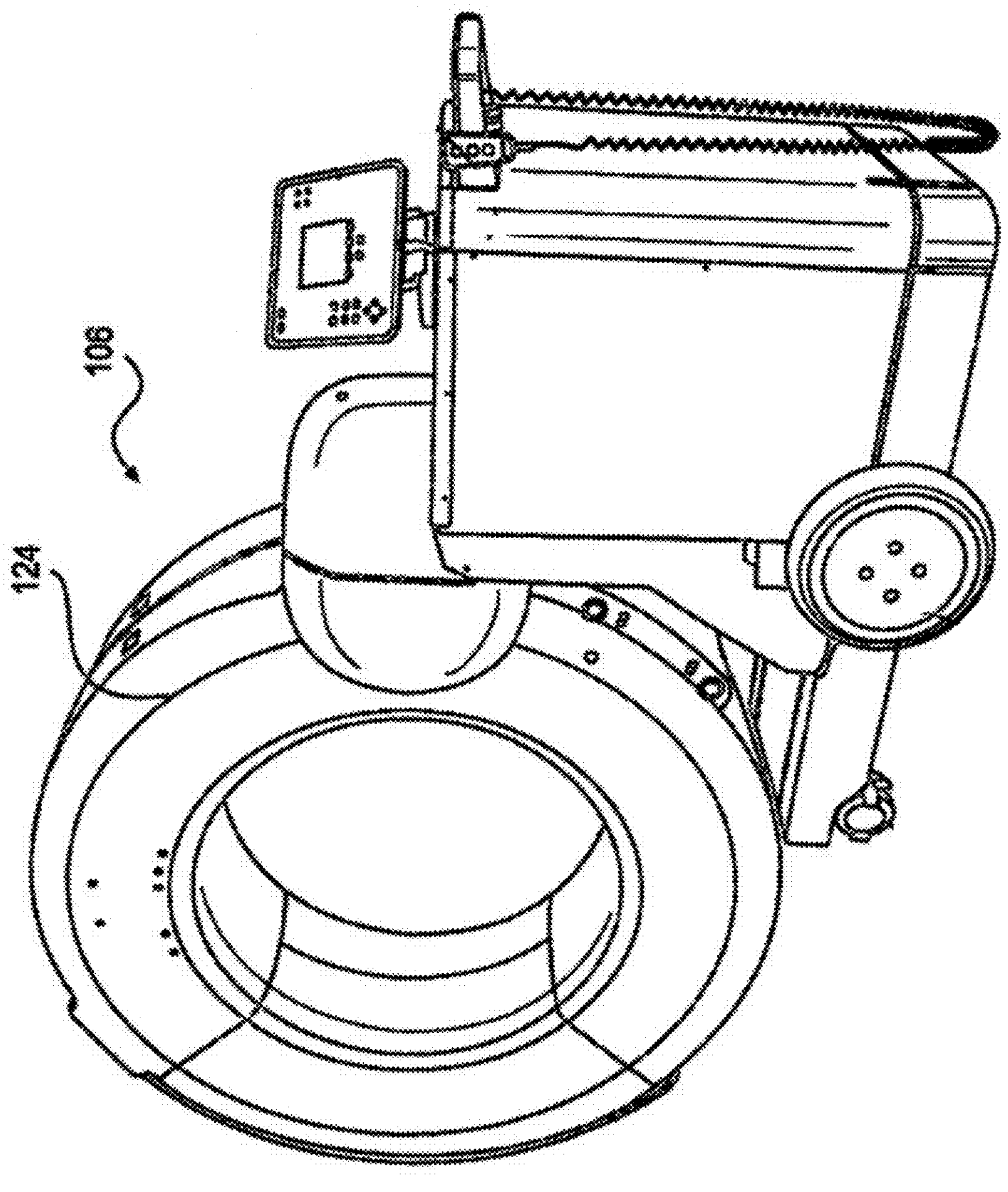
FIG. 11 illustrates an embodiment of an O-Arm imaging device that can be used in combination with the surgical robot and passive end effector in accordance with some embodiments of the present disclosure.

An automated imaging system can be used in conjunction with the surgical planning computer 910 and/or the surgical system 2 to acquire pre-operative, intra-operative, post-operative, and/or real-time image data of a patient. Example automated imaging systems are illustrated in FIGS. 10 and 11. In some embodiments, the automated imaging system is a C-arm 104 (FIG. 10) imaging device or an O-Arm® 106 (FIG. 11). (O-Arm® is copyrighted by Medtronic Navigation, Inc. having a place of business in Louisville, Colo., USA) It may be desirable to take x-rays of a patient from a number of different positions, without the need for frequent manual repositioning of the patient which may be required in an x-ray system. C-arm 104 x-ray diagnostic equipment may solve the problems of frequent manual repositioning and may be well known in the medical art of surgical and other interventional procedures. As illustrated in FIG. 10, a C-arm includes an elongated C-shaped member terminating in opposing distal ends 112 of the "C" shape. C-shaped member is attached to an x-ray source 114 and an image receptor 116. The space within C-arm 104 of the arm provides room for the physician to attend to the patient substantially free of interference from the x-ray support structure.

The C-arm is mounted to enable rotational movement of the arm in two degrees of freedom, (i.e. about two perpendicular axes in a spherical motion). C-arm is slidably mounted to an x-ray support structure, which allows orbiting rotational movement of the C-arm about its center of curvature, which may permit selective orientation of x-ray source 114 and image receptor 116 vertically and/or horizontally. The C-arm may also be laterally rotatable, (i.e. in a perpendicular direction relative to the orbiting direction to enable selectively adjustable positioning of x-ray source 114 and image receptor 116 relative to both the width and length of the patient). Spherically rotational aspects of the C-arm apparatus allow physicians to take x-rays of the patient at an optimal angle as determined with respect to the particular anatomical condition being imaged.

The O-Arm® 106 illustrated in FIG. 11 includes a gantry housing 124 which may enclose an image capturing portion, not illustrated. The image capturing portion includes an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes.

The O-Arm® 106 with the gantry housing 124 has a central opening for positioning around an object to be imaged, a source of radiation that is rotatable around the interior of gantry housing 124, which may be adapted to project radiation from a plurality of different projection angles. A detector system is adapted to detect the radiation at each projection angle to acquire object images from multiple projection planes in a quasi-simultaneous manner. The gantry may be attached to a support structure O-Arm® support structure, such as a wheeled mobile cart with wheels, in a cantilevered fashion. A positioning unit translates and/or tilts the gantry to a planned position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-Arm® 106 and C-arm 104 may be used as automated imaging system to scan a patient and send information to the surgical system 2.

Images captured by the automated imaging system can be displayed a display device of the surgical planning computer 910, the surgical robot 800, and/or another component of the surgical system 2.

Various embodiments of passive end effectors that are configured for use with a surgical system are now described in the context of FIGS. 12-19.

As will be explained in further detail below, the various passive end effectors illustrated in FIGS. 12-19 each include a base, a first planer mechanism, and a second planner mechanism. The base is configured to attach to an end effector coupler (e.g., end effector coupler 22 in FIGS. 4 and 5) of a robot arm (e.g., robot arm 18 in FIGS. 1 and 2) positioned by a surgical robot. Various clamping mechanisms may be used to firmly attach the base to the end effector coupler, removing backlash and ensuring suitable stiffness. Irreversible clamping mechanisms which may be used to attach the base to the end effector coupler can include but are not limited to toggle joint mechanisms or irreversible locking screw(s). The first mechanism extends between a rotatable connection to the base of a two and a rotatable connection to a tool attachment mechanism. The second mechanism extends between a rotatable connection to the base and a rotatable connection to the tool attachment mechanism. The first and second mechanisms pivot about the rotatable connections. The rotatable connections may be pivot joints allowing 1 degree-of-freedom (DOF) motion, universal joints allowing 2 DOF motions, or ball joints allowing 3 DOF motions. When pivot joints are used the first and second mechanisms can be configured to constrain movement of the tool attachment mechanism to a range of movement within a working plane. The tool attachment mechanism is configured to connect to a surgical saw having a saw blade that is configured to oscillate for cutting. The first and second mechanisms may be configured, e.g., via pivot joints having 1 DOF motion, to constrain a cutting plane of the saw blade to be parallel to the working plane. The tool attachment mechanism may connect to the surgical saw through various mechanisms that can include, but are not limited to, a screw, nut and bolt, clamp, latch, tie, press fit, or magnet. A DRA can be connected to the tool attachment mechanism or the surgical saw to enable tracking of a pose of the saw blade by the camera tracking system 6 (FIG. 3).

As explained above, a surgical system (e.g., surgical system 2 in FIGS. 1 and 2) includes a surgical robot (e.g., surgical robot 4 in FIGS. 1 and 2) and a tracking system (e.g., camera tracking system 6 in FIGS. 1 and 3) that is configured to determine a pose of an anatomical structure that is to be cut by the saw blade and to determine a pose of the saw blade. The surgical robot includes a robot base, a robot arm that is rotatably connected to the robot base and configured to position the passive end effector. At least one motor is operatively connected to move the robot arm relative to the robot base. At least one controller is connected to the at least one motor and configured to perform operations that include determining a pose of a target plane based on a surgical plan defining where the anatomical structure is to be cut and based on the pose of the anatomical structure, where the surgical plan may be generated by the surgical planning computer 910 of FIG. 9 based on input from an operator, e.g., surgeon or other surgery personnel. The operations further include generating steering information based on comparison of the pose of the target plane and the pose of the surgical saw. The steering information indicates where the passive end effector needs to be moved to position the working plane of the passive end effector so the cutting plane of the saw blade is aligned with the target plane.

In some further embodiments, the operations performed by the at least one controller further include controlling movement of the at least one motor based on the steering information to reposition the passive end effector so the cutting plane of the saw blade becomes aligned with the target plane and the saw blade becomes positioned a distance from the anatomical structure to be cut that is within the range of movement of the tool attachment mechanism of the passive end effector.

The operations may include providing the steering information to a display device for display to guide operator movement of the passive end effector so the cutting plane of the saw blade becomes aligned with the target plane and so the saw blade becomes positioned a distance from the anatomical structure, which is to be cut, that is within the range of movement of the tool attachment mechanism of the passive end effector.

As explained above, some surgical systems can include head-mounted display devices that can be worn by a surgeon, nurse practitioner, and/or other persons assisting with the surgical procedure. The surgical systems can display information that allows the wearer to position the passive end effector more accurately and/or to confirm that it has been positioned accurately with the saw blade aligned with the target plane for cutting a planned location on an anatomical structure. The operation to provide the steering information to the display device, may include configuring the steering information for display on a head-mounted display device having a see-through display screen that displays the steering information as an overlay on the anatomical structure that is to be cut to guide operator movement of the passive end effector so the cutting plane of the saw blade becomes aligned with the target plane and the saw blade becomes positioned the distance from the anatomical structure within the range of movement of the tool attachment mechanism of the passive end effector.

The operation to configure the steering information for display on the head-mounted display device, may include generating a graphical representation of the target plane that is displayed as an overlay anchored to and aligned with the anatomical structure that is to be cut, and generating another graphical representation of the cutting plane of the saw blade that is displayed as an overlay anchored to and aligned with the saw blade. A wearer may thereby move the surgical saw to provide visually observed alignment between the graphically rendered target plane and the graphically rendered cutting plane.

The operation to configure the steering information for display on the head-mounted display device, may include generating a graphical representation a depth of cut made by the saw blade into a graphical representation of the anatomical structure being cut. Thus, the wearer can use the graphical representation of depth of cut to better monitor how the saw blade is cutting through bone despite direct observation of the cutting being obstructed by tissue or other structure.

The tracking system can be configured to determine the pose of the anatomical structure that is to be cut by the saw blade based on determining a pose of tracking markers, e.g., DRAs, that are attached to the anatomical structure, and can be configured to determine a pose of the surgical saw based on determining a pose of tracking markers connected to at least one of the surgical saw and the passive end effector. The tracking system can be configured to determine the pose of the surgical saw based on rotary position sensors which are configured to measure rotational positions of the first and second mechanisms during movement of the tool attachment mechanism within the working plane. As explained above, position sensors may be directly connected to at least one joint of the passive end effector structure, but may also be positioned in another location in the structure and remotely measure the joint position by interconnection of a timing belt, a wire, or any other synchronous transmission interconnection. Additionally the pose of the saw blade can be determined based on the tracking markers attached to the structure base, position sensors in the passive structure and kinematic model of the structure.

Figure 12:
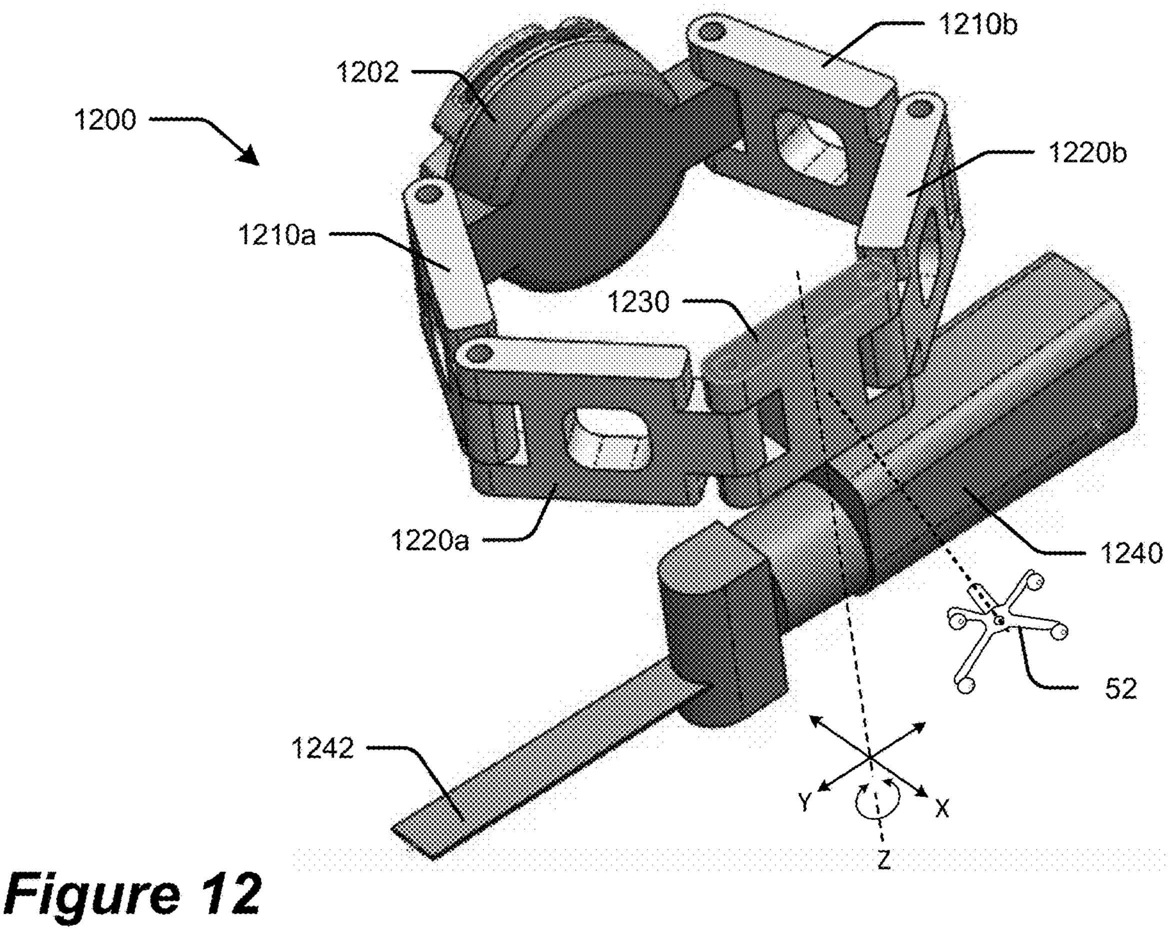
FIGS. 12-19 illustrate alternative embodiments of passive end effectors which are configured in accordance with some embodiments of the present disclosure.

The various passive end effectors disclosed herein can be sterilizable or non-sterile (covered by a sterile drape) passive 3DOF (Degree Of Freedom) mechanical structures allowing mechanical guidance of a surgical saw, such as a sagittal saw, along two translations in a plane parallel to the saw blade (defining the cut plane), and one rotation perpendicular to this cut plane (instrument orientation). During the surgery, the surgical robot 4 moves the end effector coupler 22, and the passive end effector and surgical saw attached there, automatically to a position close to a knee or other anatomical structure, so that all bone to be cut is within the workspace of the passive end effector. This position depends on the cut to be made and the surgery planning and implant construction. The passive end effector can have 3 DOF to guide sagittal saw on the cutting plane providing two translation (X and Y directions) and a rotation (around Z axis) as shown in FIG. 12.

When the surgical robot 4 achieves a planned position, it holds the position (either on brakes or active motor control) and does not move during the particular bone cut. It is the passive end effector that allows movement of the saw blade of the surgical saw along the planned target plane. Such planar cuts are particularly useful for classical total knee arthroplasty where all bone cuts are planar. In partial knee arthroplasty there are special types of implants, called "on-lay" which can be in conjunction with saw-prepared bone surfaces. The various passive end effectors have mechanical structure that can ensure precision of guidance during cuts, with higher precision than classical jigs, and provide sufficient range of workspace range to cut all the bone that is planned and while provide sufficient transverse stiffness (corresponding to locked DOF) despite possibly significant amount of vibrations originating from the surgical saw in addition to forces applied by the surgeon and bone reactionary forces.

As the same time, it is preferable to measure the passive end effector position because it enables the surgical robot 4 to inform the surgeon how much bone has been removed (procedure advancement). One way to provide real-time information on bone removal is for the surgical robot 4 to measure where the saw blade passed in reference to the bone because the blade can pass only where the bone has been cut. To measure sawblade position a DRA can be mounted to the surgical saw and/or the passive end effector. This enables direct or indirect measurement of the saw position in 3D space. An alternative way to measure saw blade position is to integrate position (rotation or translation) sensors (e.g. encoders, resolvers) into position information of the passive end effector in order to calculate position of the saw blade using a mathematical model of a defined relationship between location of the passive end effector geometry and the saw blade.

In one embodiment, a conventional sagittal saw mechanism can be used with the surgical system computer platform 900 with little or no changes. The potential changes would involve adapting an external shield to enable easy attachment of the surgical saw to the passive end effector but would not necessarily involve changes in the internal mechanics. The passive end effector may be configured to connect to a conventional sagittal saw provided by, for example, DeSoutter company.

To prevent the saw from unintentional passive end effector movement when the surgical robot 4 positions the passive end effector, e.g., to prevent the surgical saw from falling on the patient due to gravitational forces, the passive end effector can include a lock mechanism that moves between engaged and disengaged operations. While engaged, the lock mechanism prevents movement of the saw blade with respect to the robot end effector coupler, either directly by locking the degree of freedoms (DOFs) of the surgical saw, or indirectly by braking or locking specifics joints of the passive end effector. While disengaged, the first and second mechanisms of the passive end effector can be moved relative to the base without interference from the lock mechanism. The lock mechanism may also be used when a surgeon holds the surgical saw and controls the surgical robot 4 movement by applying forces and torques to the surgical saw. The surgical robot 4, using the load cell 64 of FIGS. 6 and 7 integrated in the distal end of the robot arm 22, measures forces and torques that are applied and generates responsive forces and torques on the robot arm 22 so the surgeon can more easily move the passive end effector back and forth, left and right, apply rotations around various axes.

A first embodiment of a passive end effector is shown in FIG. 12. Referring FIG. 12, the passive end effector 1200 includes a base 1202 configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1200 further includes first and second mechanisms that extend between rotatable connections to the base 1202 and rotatable connections to a tool attachment mechanism. The rotatable connections may be pivot joints allowing 1 degree-of-freedom (DOF) motion, universal joints allowing 2 DOF motions, or ball joints allowing 3 DOF motions. The first and second mechanisms form a parallel architecture that positions the surgical saw rotation axis in the cut plane.

First and second link segments 1210*a* and 1220*a* form the first planer mechanism, and third and fourth link segments 1210*b* and 1220*b* form the second planner mechanism. The first link segment 1210*a* extends between a rotatable connection to a first location on the base 1202 and a rotatable connection to an end of the second link segment 1220*a*. The third link segment 1210*b* extends between a rotatable connection to a second location on the base 1202 and a rotatable connection to an end of the fourth link segment 1220*b*. The first and second locations on the base 1202 are spaced apart on opposite sides of a rotational axis of the base color to when rotated by the robot arm. The tool attachment mechanism is formed by a fifth link segment that extends between rotatable connections to distal ends of the second link segment 1220*a* and the fourth link segment 1220*b* relative to the base 1202. The first and second mechanisms (first and second link segments 1210*a*-1220*a* and third and fourth link segments 1210*b*-1220*b*) pivot about their rotatable connections to constrain movement of the tool attachment mechanism 1230 to a range of movement within a working plane. The tool attachment mechanism 1230 is configured to connect to a surgical saw 1240 having a saw blade 1242 that is configured to oscillate for cutting. The first and second mechanisms (first and second link segments 1210*a*-1220*a* and third and fourth link segments 1210*b*-1220*b*) may be configured, e.g., via pivot joints having 1 DOF motion, to constrain a cutting plane of the saw blade 1242 to be parallel to the working plane. The tool attachment mechanism 1230 may connect to the surgical saw 1240 through various mechanisms that can include, but are not limited to, a screw, nut and bolt, clamp, latch, tie, press fit, or magnet. A DRA 52 can be connected to the tool attachment mechanism 1230 or the surgical saw 1240 to enable tracking of a pose of the saw blade 1242 by the camera tracking system 6 (FIG. 3).

The passive end effector 1200 provides passive guidance of the surgical saw 1240 to constrain the saw blade 1242 to a defined cutting plane and reduce its mobility to three degrees of freedom (DOF): two translations Tx and Ty in a plane parallel to the cutting plane of the saw blade 1242; and one rotational Rz around an axis perpendicular to the cutting plane.

In some embodiments, a tracking system is configured to determine the pose of the saw blade 1242 based on rotary position sensors connected to the rotational joints of at least some of the link segments of the passive end effector 1200. The rotary position sensors are configured to measure rotational positions of the joined link segments during movement of the tool attachment mechanism within the working plane. For example, a rotary position sensor can be configured to measure rotation of the first link segment 1210*a* relative to the base 1202, another rotary position sensor can be configured to measure rotation of the second link segment 1220*a* relative to the first link segment 1210*a*, and another rotary position sensor can be configured to measure rotation of the tool attachment mechanism 1230 relative to the second link segment 1220*a*. The surgical saw 1240 can connected to have a fixed orientation relative to the tool attachment mechanism 1230. A serial kinematic chain of the passive end effector 1200 connecting the saw blade 1242 and the robot arm 22, having serialized link segments and pivoting joints, provides the required mobility to the surgical saw 1240. The position of the tip of the saw blade 1242 in the plane defined by the passive kinematic chain can be fully determined by the joint angles, sensed through the rotary position sensors, and the structural geometry of the interconnected link segments. Therefore, by measuring the relative angle between each connected link segment, for example along one or more interconnected paths between the base 1202 and the surgical saw 1240, the position of the tip of the saw blade 1242 in the cut space can be computed using the proposed forward kinematic model. When the position and orientation of robot arm 22 distal end position and orientation with respect to the bone is known, the position and orientation of the saw blade 1242 with respect to the bone can be computed and displayed as feedback to the surgeon.

Example types of rotary position sensors that can be used with passive end effectors herein can include, but are not limited to: potentiometers; optical; capacitive; rotary variable differential transformer (RVDT); linear variable differential transformer (LVDT); Hall effect; and incoder.

A potentiometer based sensor is a passive electronic component. Potentiometers work by varying the position of a sliding contact across a uniform resistance. In a potentiometer, the entire input voltage is applied across the whole length of the resistor, and the output voltage is the voltage drop between the fixed and sliding contact. To receive and absolute position, a calibration-position is needed. Potentiometers may have a measurement range smaller 360°.

An optical encoder can include a rotating disk, a light source, and a photo detector (light sensor). The disk, which is mounted on the rotating shaft, has patterns of opaque and transparent sectors coded into the disk. As the disk rotates, these patterns interrupt the light emitted onto the photo detector, generating a digital or pulse signal output. Through signal encoding on the disk absolute and relative as well as multi-turn measurements are possible.

A capacitive encoder detects changes in capacitance using a high-frequency reference signal. This is accomplished with the three main parts: a stationary transmitter, a rotor, and a stationary receiver. Capacitive encoders can also be provided in a two-part configuration, with a rotor and a combined transmitter/receiver. The rotor can be etched with a sinusoidal pattern, and as it rotates, this pattern modulates the high-frequency signal of the transmitter in a predictable way. The encoder can be multi-turn, but absolute measurement is difficult to realize. Calibration at startup is needed.

RVDT and LVDT sensors operate where the core of the transformer is in null position, the output voltages of the two, primary and secondary, windings are equal in magnitude, however opposite in direction. The overall output of the null position is always zero. An angular displacement from the null position is inducing a total differential output voltage. Therefore, the total angular displacement is directly proportional to the linear differential output voltage. The differential output voltages increase with clockwise and decrease with anti-clockwise direction. This encoder works in absolute measurement and may not be multi-turn compatible. Calibration during assembly is needed.

In a Hall effect sensors, a thin strip of metal has a current applied along it. In the presence of a magnetic field, the electrons in the metal strip are deflected toward one edge, producing a voltage gradient across the short side of the strip, i.e., perpendicular to the feed current. In its simplest form, the sensor operates as an analog transducer, directly returning a voltage. With a known magnetic field, its distance from the Hall plate can be determined. Using groups of sensors, the relative position of the magnet can be deduced. By combining multiple sensor elements with a patterned magnet-plate, position can be detected absolute and relative similar to optical encoders.

An incoder sensor works in a similar way to rotary variable transformer sensor, brushless resolvers or synchros. The stator receives DC power and produces a low power AC electromagnetic field between the stator and rotor. This field is modified by the rotor depending on its angle. The stator senses the resulting field and outputs the rotation angle as an analogue or digital signal. Unlike resolvers, incoders use laminar circuits rather than wound wire spools. This technology enables incoders compact form, low mass, low inertia and high accuracy without high precision installation. A signal (Z) to count one full rotation is transmitted. Multi-turn and absolute sensing is possible.

Figure 13:
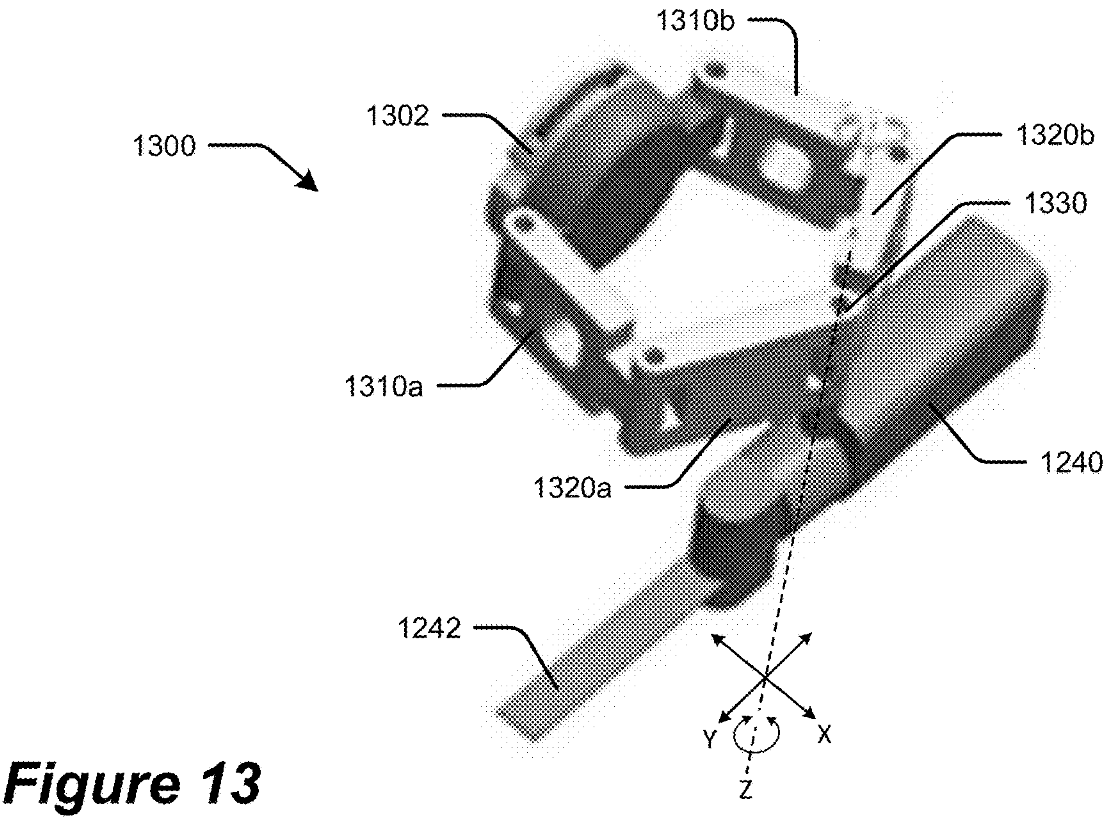

A second embodiment of a passive end effector is shown in FIG. 13. Referring to FIG. 13, the passive end effector 1300 includes a base 1302 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1300 further includes first and second mechanisms that extend between rotatable connections to the base 1302 and rotatable connections to a tool attachment mechanism. The rotatable connections may be pivot joints allowing 1 DOF motion, universal joints allowing 2 DOF motions, or ball joints allowing 3 DOF motions. First and second link segments 1310*a* and 1320*a* form the first planer mechanism, and third and fourth link segments 1310*b* and 1320*b* form the second planner mechanism. The first link segment 1310*a* extends between a rotatable connection to a first location on the base 1302 and a rotatable connection to an end of the second link segment 1320*a*. The third link segment 1310*b* extends between a rotatable connection to a second location on the base 1302 and a rotatable connection to an end of the fourth link segment 1320*b*. The first and second locations on the base 1302 are spaced apart on opposite sides of a rotational axis of the base color to when rotated by the robot arm. Distal ends of the second link segment 1320*a* and the fourth link segment 1320*b* from the base 1302 are rotatably connected to each other and to the tool attachment mechanism 1330. The first and second mechanisms (first and second link segments 1310*a*-1320*a* and third and fourth link segments 1310*b*-1320*b*) may be configured, e.g., via pivot joints having 1 DOF motion, to rotate about their rotatable connections to constrain movement of the tool attachment mechanism 1330 to a range of movement within a working plane. The tool attachment mechanism 1330 is configured to connect to a surgical saw 1240 having a saw blade 1242 that is configured to oscillate for cutting. The first and second mechanisms (first and second link segments 1310*a*-1320*a* and third and fourth link segments 1310*b*-1320*b*) constrain a cutting plane of the saw blade 1242 to be parallel to the working plane. The tool attachment mechanism 1330 may connect to the surgical saw 1240 through various mechanisms that can include, but are not limited to, a screw, nut and bolt, clamp, latch, tie, press fit, or magnet. A DRA can be connected to the tool attachment mechanism 1330 or the surgical saw 1240 to enable tracking of a pose of the saw blade 1242 by the camera tracking system 6 (FIG. 3).

Figure 14:
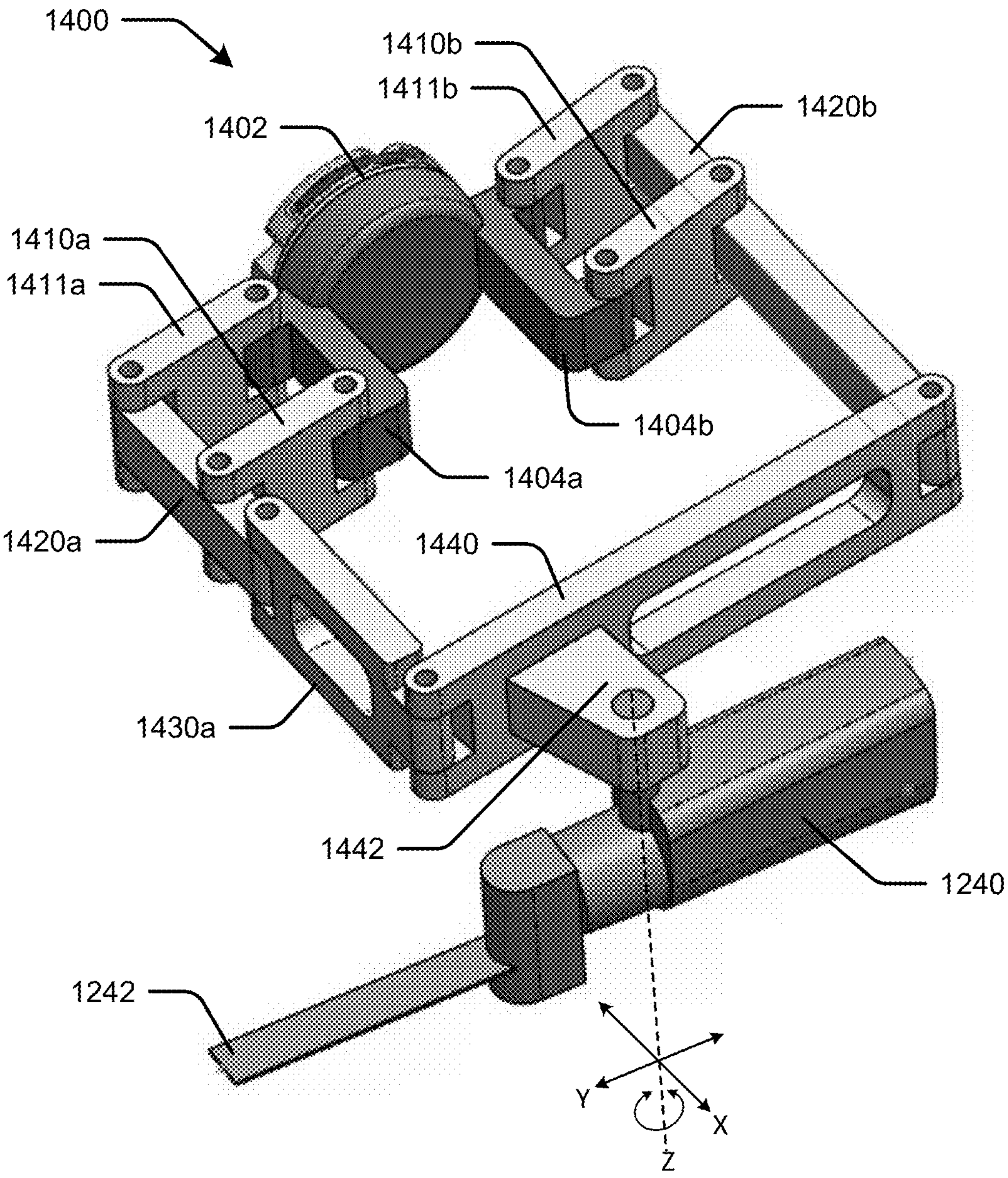

A third embodiment of a passive end effector is shown in FIG. 14. Referring to FIG. 14, the passive end effector 1400 includes a base 1402 that is configured to attach to an end effector coupler (e.g., end effector coupler 22 in FIGS. 4 and 5) of a robot arm (e.g., robot arm 18 in FIGS. 1 and 2) positioned by a surgical robot. The base 1402 includes first and second elongated base segments 1404*a* and 1404*b* that extend from spaced apart locations on opposite sides of a rotational axis of the base 1402 when rotated by the robot arm. The first and second elongated base segments 1404*a* and 1404*b* extend in a direction away from the end effector coupler of the robot arm when attached to the passive end effector 1400. The passive end effector 1400 further includes first and second mechanisms that extend between rotatable connections to the elongated base segments 1404*a* and 1404*b* and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions.

The first mechanism includes a first link segment 1411*a*, the second link segment 1410*a*, a third link segment 1420*a*, and a fourth link segment 1430*a*. The first and second link segments 1411*a* and 1410*a* extend parallel to each other between rotatable connections to spaced apart locations on the first elongated base segment 1404*a* and spaced apart locations on the third link segment 1420*a*. An end of the third link segment 1420*a* is rotatably connected to an end of the fourth link segment 1430*a*.

The second mechanism includes a fifth link segment 1411*b*, a sixth link segment 1410*b*, and a seventh link segment 1420*b*. The fifth and sixth link segments 1411*b* and 1410*b* extend parallel to each other between rotatable connections to spaced apart locations on the second elongated base segment 1404*b* and spaced apart locations on the seventh link segment 1420*b*. The tool attachment mechanism includes an eighth link segment 1440 that extends between rotatable connections to distal ends of the fourth and seventh link segments 1430*a* and 1420*b* from the base 1402. In a further embodiment, the eighth link segment 1440 of the tool attachment mechanism includes an attachment member 1442 that extends in a direction away from the base 1402 to a rotatable connector that is configured to connect to the surgical saw 1240. The attachment member 1442 extends from a location on the eighth link segment 1440 that is closer to the fourth link segment 1430*a* than to the seventh link segment 1420*b*.

The first and second mechanisms (set of link segments 1411*a*, 1410*a*, 1420*a*, 1430*a* and set of link segments 1411*b*, 1410*b*, 1420*b*) may be configured to pivot about their rotatable connections to constrain movement of the tool attachment mechanism 1440 to a range of movement within a working plane. The tool attachment mechanism 1440 is configured to connect to the surgical saw 1240 having the saw blade 1242 that is configured to oscillate for cutting. The first and second mechanisms may be configured, e.g., via pivot joints having 1 DOF motion, to constrain a cutting plane of the saw blade 1242 to be parallel to the working plane. The tool attachment mechanism 1440 may connect to the surgical saw 1240 through various mechanisms that can include, but are not limited to, a screw, nut and bolt, clamp, latch, tie, press fit, or magnet. A DRA can be connected to the tool attachment mechanism 1440, such as to the attachment member 1442, or the surgical saw 1240 to enable tracking of a pose of the saw blade 1242 by the camera tracking system 6 (FIG. 3).

The passive end effector 1400 of FIG. 14 has a parallel architecture enabling positioning of the surgical saw about a rotation axis in the cut plane. Synchronized and/or different motion of lateral parallelograms allow positioning of the surgical saw rotation axis in the cut plane.

Figure 15:
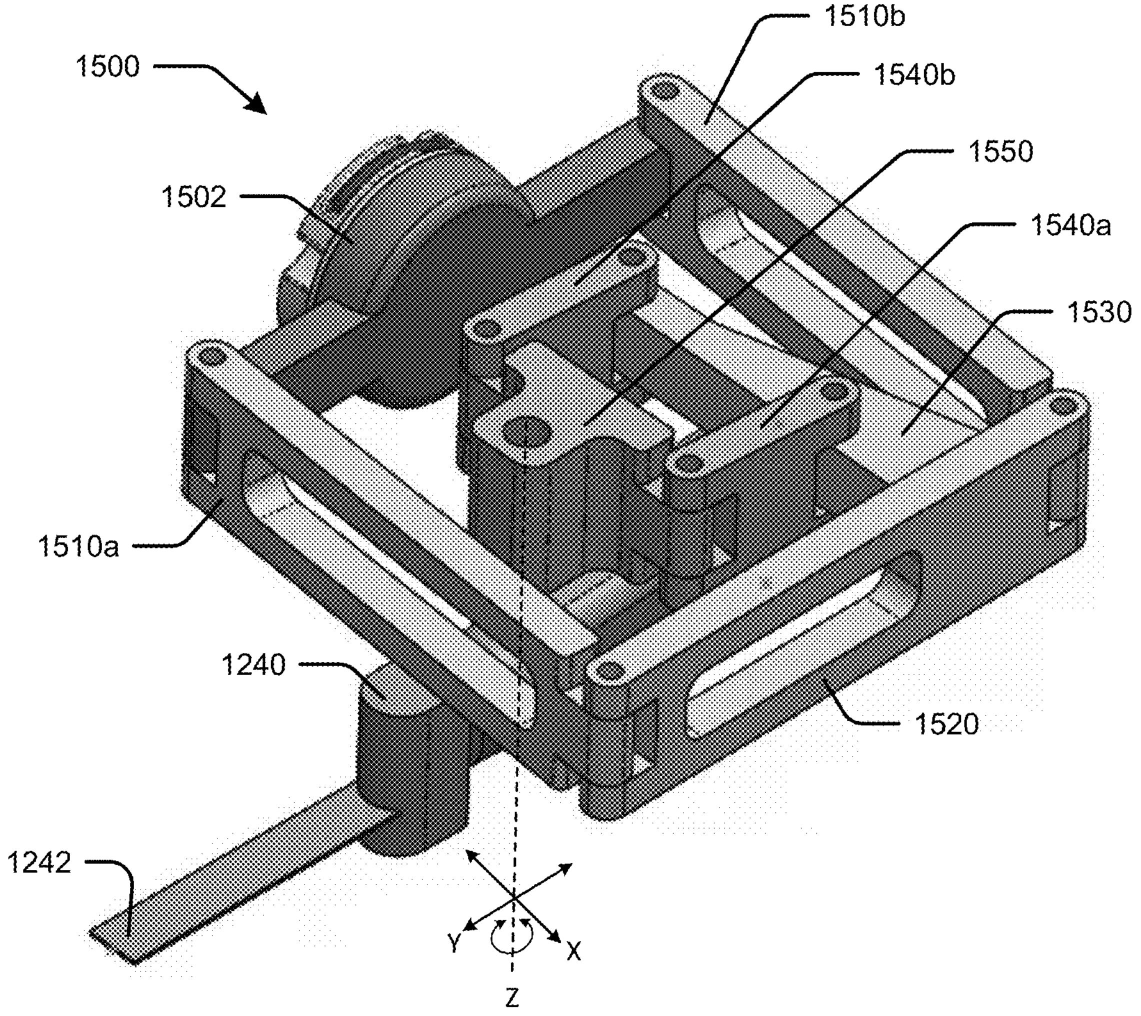

A fourth embodiment of a passive end effector is shown in FIG. 15. The passive end effector 1500 includes a base

1502 that is configured to attach to an end effector coupler (e.g., end effector coupler 22 in FIGS. 4 and 5) of a robot arm (e.g., robot arm 18 in FIGS. 1 and 2) positioned by a surgical robot. The base 1502 may include first and second elongated base segments that extend from spaced apart locations on opposite sides of a rotational axis of the base 1502 when rotated by the robot arm. The first and second elongated base segments extend away from each other. The passive end effector 1500 further includes first and second mechanisms that extend between rotatable connections to the base 1502 and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions.

The first mechanism includes a first link segment 1510*a*. The second mechanism includes a second segment 1510*b*. The tool attachment mechanism includes a third link segment 1520, a fourth link segment 1530, a fifth link segment 1540*a*, a sixth link segment 1540*b*, and a seventh link segment 1550. The first and second link segments 1510*a* and 1510*b* extend between rotatable connections to first and second locations, respectively, on the base 1502, e.g., to first and second elongated base segments extending away from the base 1502, to rotatable connections at opposite ends of the third link segment 1520. The first and second locations on the base 1502 are spaced apart on opposite sides of a rotational axis of the base when rotated by the robot arm. The fourth link segment 1530 extends from the third link segment 1520 in a direction towards the base 1502. The fifth and sixth link segments 1540*a* and 1540*b* extend parallel to each other between rotatable connections to spaced apart locations on the fourth link segment 1530 and spaced apart locations on the seventh link segment 1550. The seventh link segment 1550 is configured to have a rotatable connector that is configured to connect to the surgical saw 1240.

The first through sixth link segments 1510*a-b*, 1520, 1530, and 1540*a-b* may be configured to pivot about their rotatable connections to constrain movement of the seventh link segment 1550 to a range of movement within a working plane. The seventh link segment 1550 is configured to connect to the surgical saw 1240 having the saw blade 1242 that is configured to oscillate for cutting. The first through sixth link segments 1510*a-b*, 1520, 1530, and 1540*a-b* may be configured to constrain a cutting plane of the saw blade 1242 to be parallel to the working plane, e.g., via pivot joints having 1 DOF motion. The seventh link segment 1550 may connect to the surgical saw 1240 through various mechanisms that can include, but are not limited to, a screw, nut and bolt, clamp, latch, tie, press fit, or magnet. A DRA can be connected to the seventh link segment 1550 or the surgical saw 1240 to enable tracking of a pose of the saw blade 1242 by the camera tracking system 6 (FIG. 3).

Figure 16:
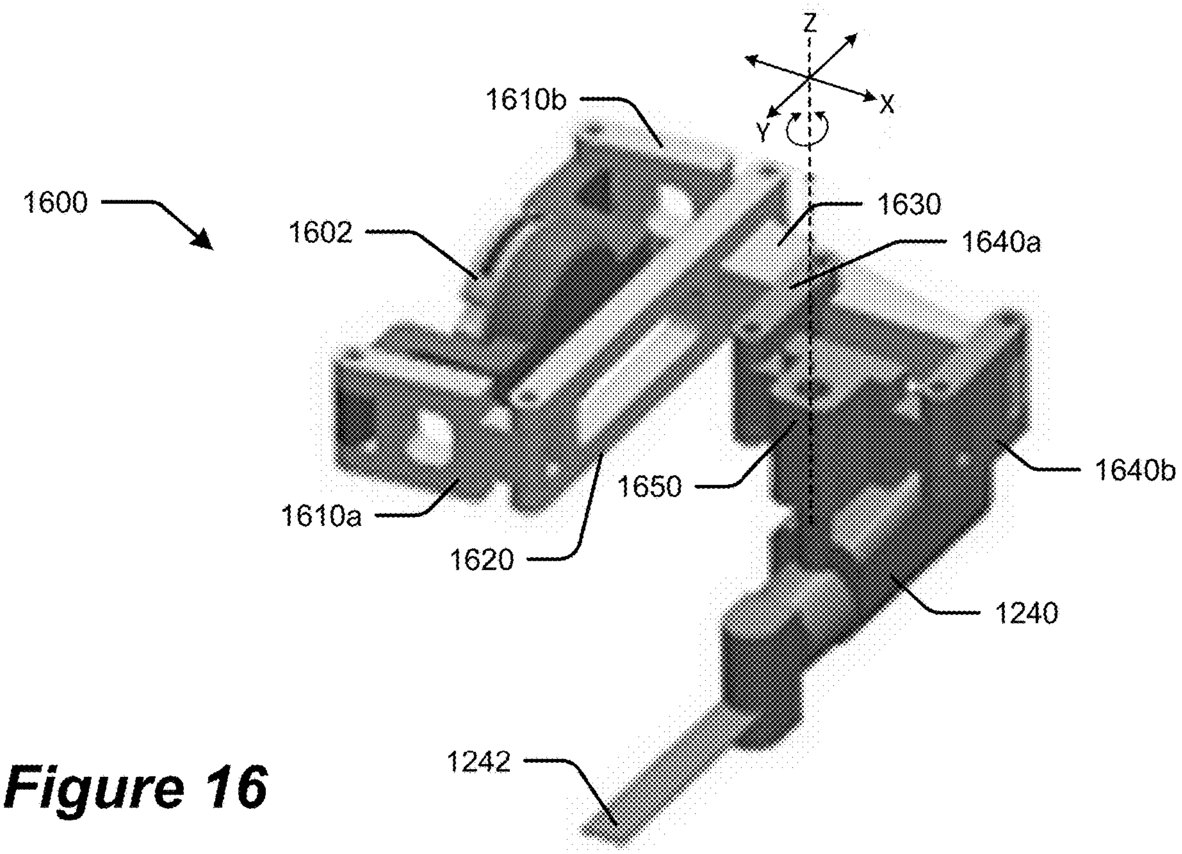

A fifth embodiment of a passive end effector is shown in FIG. 16. The passive end effector 1600 includes a base 1602 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1600 further includes first and second mechanisms that extend between rotatable connections to the base 1502 and rotatable connections to a tool attachment mechanism. The first mechanism includes a first link segment 1610*a*. The second mechanism includes a second segment 1610*b*. The tool attachment mechanism includes a third link segment 1620, a fourth link segment 1630, a fifth link segment 1640*a*, a sixth link segment 1640*b*, and a seventh link segment 1650. One or more of the rotatable connections disclosed for this embodiment may be pivot joints allowing 1 DOF motion, universal joints allowing 2 DOF motions, or ball joints allowing 3 DOF motions.

The first and second link segments 1610*a* and 1610*b* extend between rotatable connections to first and second locations, respectively, on the base 1602 to rotatable connections at opposite ends of the third link segment 1620. The first and second locations on the base 1602 are spaced apart on opposite sides of a rotational axis of the base 1602 when rotated by the robot arm. The fourth link segment 1630 extends from the third link segment 1620 in a direction away from the base 1602. The fifth and sixth link segments 1640*a* and 1640*b* extend parallel to each other between rotatable connections to spaced apart locations on the fourth link segment 1630 and spaced apart locations on the seventh link segment 1650. The seventh link segment 1650 is configured to have a rotatable connector that is configured to connect to the surgical saw 1240.

The first through sixth link segments 1610*a-b*, 1620, 1630, and 1640*a-b* may be configured to pivot about their rotatable connections to constrain movement of the seventh link segment 1650 to a range of movement within a working plane. The seventh link segment 1650 is configured to connect to the surgical saw 1240 having the saw blade 1242 that is configured to oscillate for cutting. The first through sixth link segments 1610*a-b*, 1620, 1630, and 1640*a-b* may be configured to pivot while constraining a cutting plane of the saw blade 1242 to be parallel to the working plane. The seventh link segment 1650 may connect to the surgical saw 1240 through various mechanisms that can include, but are not limited to, a screw, nut and bolt, clamp, latch, tie, press fit, or magnet. A DRA can be connected to the seventh link segment 1650 or the surgical saw 1240 to enable tracking of a pose of the saw blade 1242 by the camera tracking system 6 (FIG. 3).

The passive end effector 1600 provides two perpendicular translational movements for positioning the surgical saw rotation axis in the cutting plane, and where the two translations are implemented by parallelograms.

Figure 17:
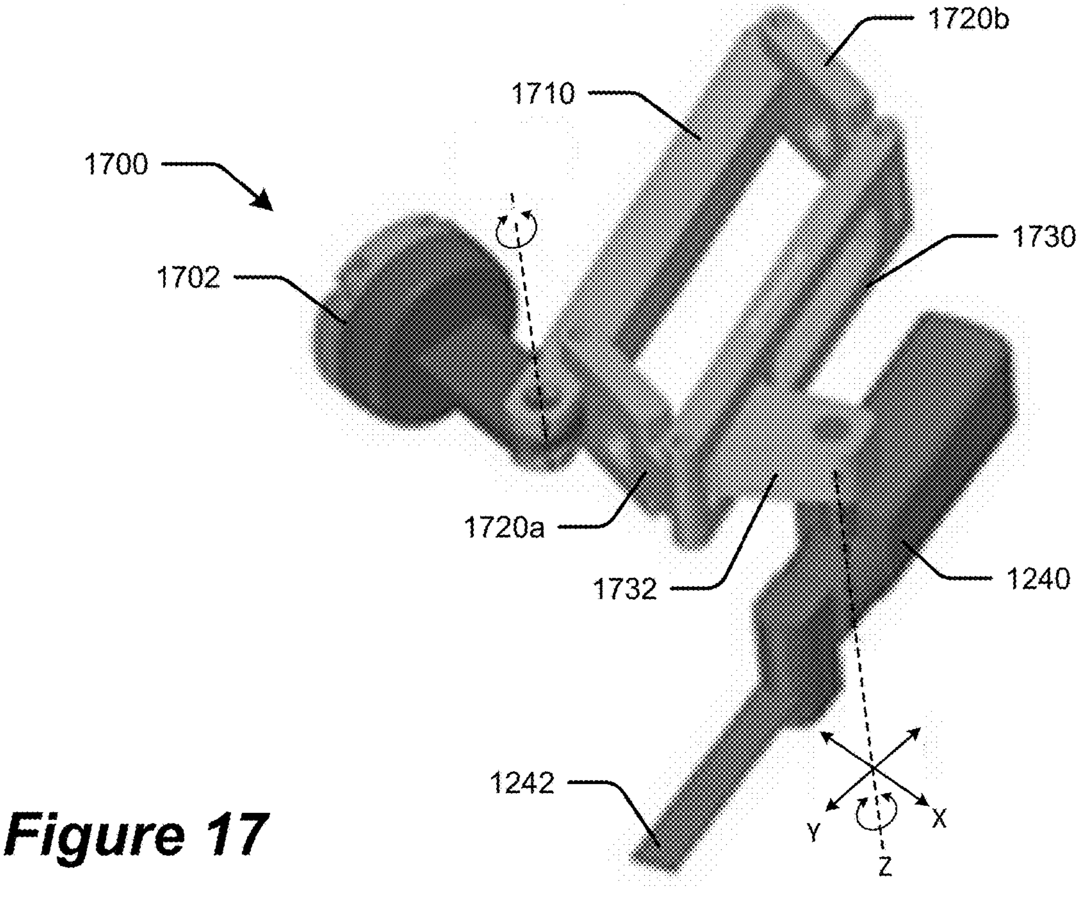

A sixth embodiment of a passive end effector is shown in FIG. 17. The passive end effector 1700 includes a base 1702 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1700 further includes first and second mechanisms that extend between rotatable connections to the base 1702 and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions. The first and second mechanisms are connected to provide translation along the radius of a parallelogram. The first mechanism includes first and second link segments 1710 and 1720*b*. The first link segment 1710 extends between a rotatable connection to the base 1702 and a rotatable connection to an end of the second link segment 1720*b*. The second mechanism includes a third link segment 1720*a*. The tool attachment mechanism includes a fourth link segment 1730. The second and third link segments 1720*b* and 1720*a* extend away from the base 1702 and parallel to each other between rotatable connections to spaced apart locations on the first link segment 1710 and spaced apart locations on the fourth link segment 1730. The fourth link segment 1730 comprises an attachment member 1732 that extends in a direction away from the base to a rotatable connector that is configured to connect to the surgical saw 1240. The attachment member

1732 extends from a location on the fourth link segment 1730 that is closer to the third link segment 1720*a* than to the second link segment 1720*b*.

The first through third link segments 1710, 1720*b*, 1720*a* may be configured to pivot about their rotatable connections to constrain movement of the fourth link segment 1730 to a range of movement within a working plane. The fourth link segment 1730 is configured to connect to the surgical saw 1240 having the saw blade 1242 that is configured to oscillate for cutting. The first through third link segments 1710, 1720*b*, 1720*a* pivot and may be configured to constrain a cutting plane of the saw blade 1242 to be parallel to the working plane. The fourth link segment 1730, e.g., the attachment member 1732 thereof, may connect to the surgical saw 1240 through various mechanisms that can include, but are not limited to, a screw, nut and bolt, clamp, latch, tie, press fit, or magnet. A DRA can be connected to the fourth link segment 1730, e.g., to the attachment member 1732, or the surgical saw 1240 to enable tracking of a pose of the saw blade 1242 by the camera tracking system 6 (FIG. 3).

Figure 18:
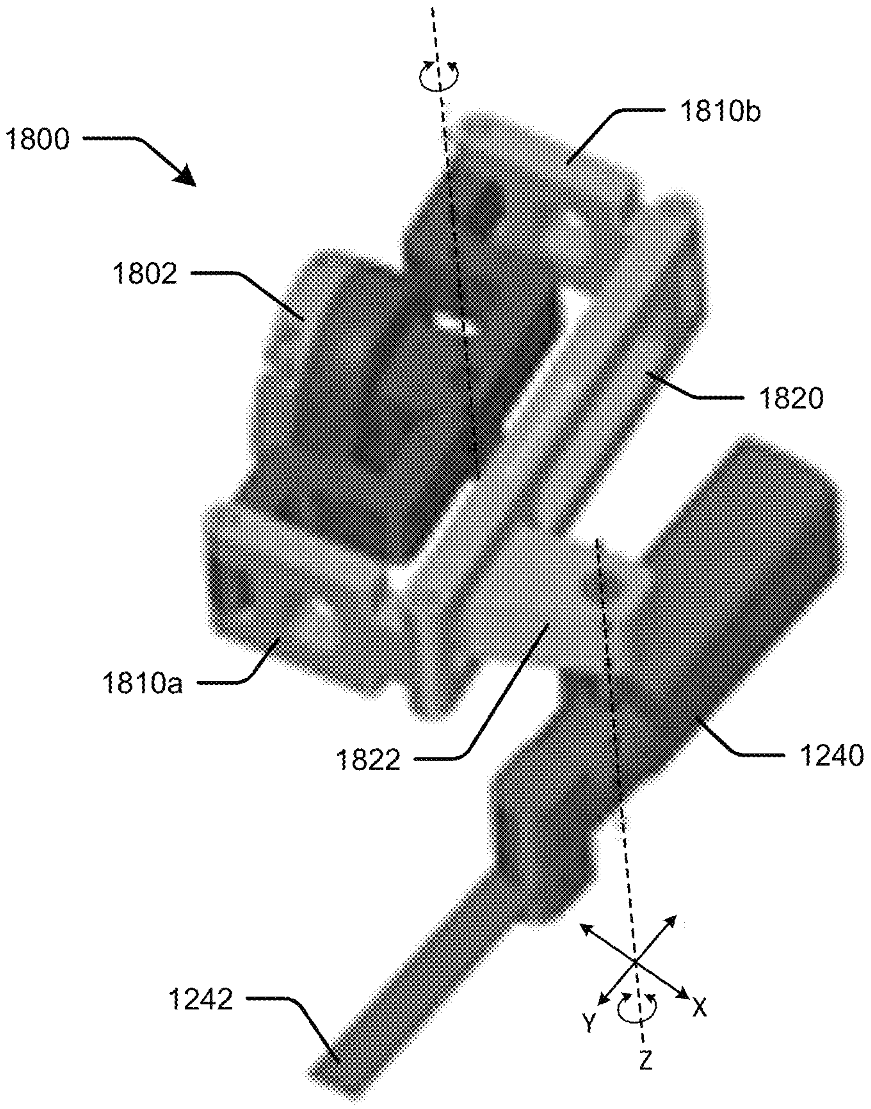

A seventh embodiment of a passive end effector is shown in FIG. 18. The passive end effector 1800 includes a base 1802 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1800 further includes first and second mechanisms that extend between rotatable connections to the base 1802 and rotatable connections to a tool attachment mechanism. One or more of the rotatable connections disclosed for this embodiment may be pivot joints allowing 1 DOF motion, universal joints allowing 2 DOF motions, or ball joints allowing 3 DOF motions. The first mechanism includes a first link segment 1810*a*. The second mechanism includes a second link segment 1810*b*. The tool attachment mechanism includes a third link segment 1820. The first and second link segments 1810*a* and 1810*b* extend between rotatable connections to first and second locations, respectively, on the base 1802 to rotatable connections at opposite ends of the third link segment 1820. The first and second locations on the base 1802 are spaced apart on opposite sides of a rotational axis of the base 1802 when rotated by the robot arm. The third link segment 1820 includes an attachment member 1822 that extends in a direction away from the base 1802 to a rotatable connector that is configured to connect to the surgical saw 1240. The attachment member 1822 extends from a location on the third link segment 1820 that is closer to the first link segment 1810*a* than to the second link segment 1810*b*. One or more of the rotatable connections disclosed for this embodiment may be pivot joints allowing 1 DOF motion, universal joints allowing 2 DOF motions, or ball joints allowing 3 DOF motions.

The first and second link segments 1810*a* and 1810*b* may be configured to pivot about their rotatable connections between the base 1802 and the third link segment 1820 to constrain movement of the attachment member 1822 to a range of movement within a working plane. In some other embodiments one or more of the rotatable connections can be universal joints allowing 2 DOF motions or ball joints allowing 3 DOF motions such that the movement is not constrained to the working plane. The attachment member 1822 is configured to connect to the surgical saw 1240 having the saw blade 1242 that is configured to oscillate for cutting. The first and second link segments 1810*a* and 1810*b* pivot while constraining a cutting plane of the saw blade 1242 to be parallel to the working plane. The attachment member 1822 may connect to the surgical saw 1240 through various mechanisms that can include, but are not limited to, a screw, nut and bolt, clamp, latch, tie, press fit, or magnet. A DRA can be connected to the third link segment 1820, e.g., to the attachment member 1822, or the surgical saw 1240 to enable tracking of a pose of the saw blade 1242 by the camera tracking system 6 (FIG. 3).

Figure 19:
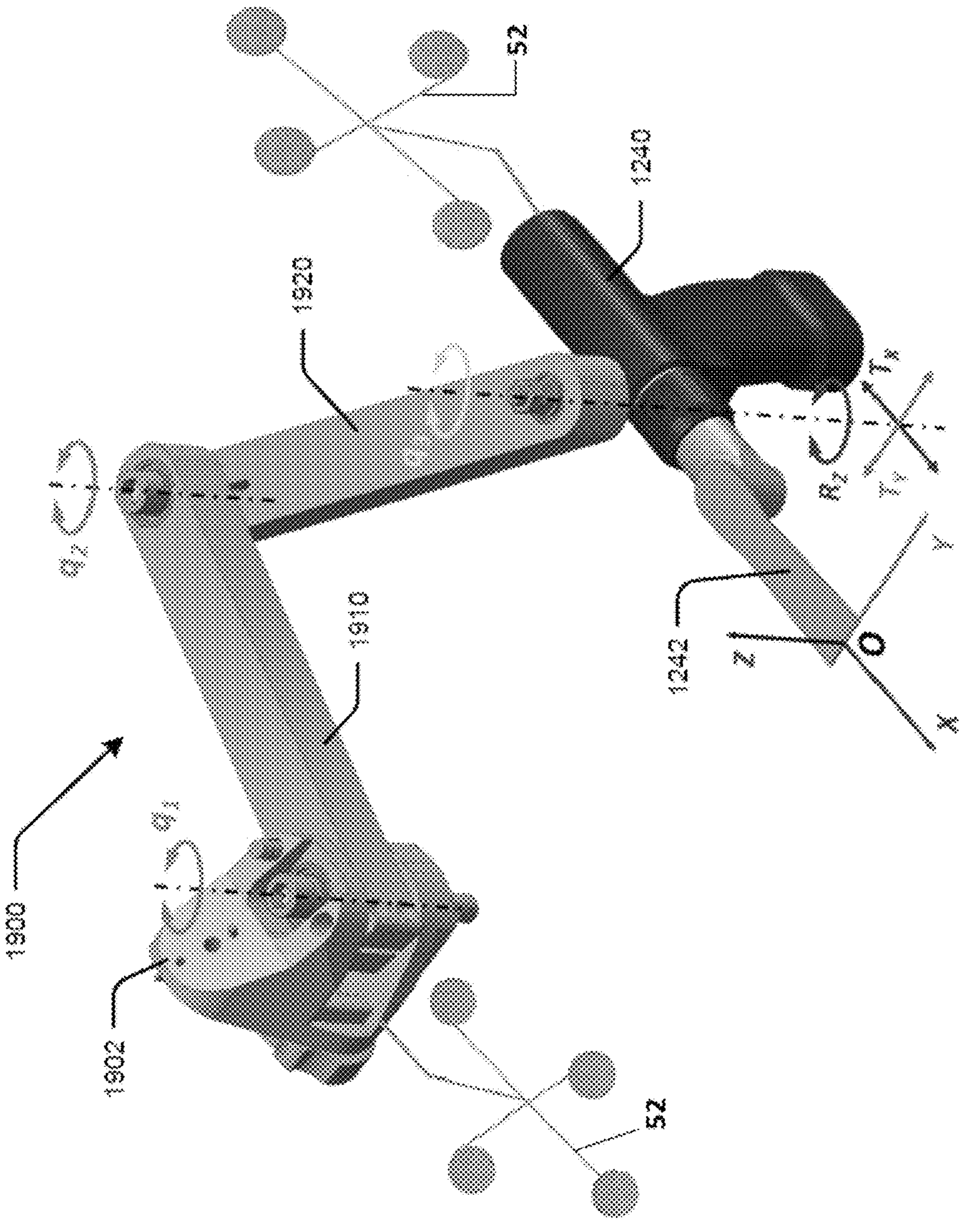

An eighth embodiment of a passive end effector is shown in FIG. 19. The passive end effector 1900 includes a base 1902 that is configured to attach to an end effector coupler (e.g., end effector coupler 22 in FIGS. 4 and 5) of a robot arm (e.g., robot arm 18 in FIGS. 1 and 2) positioned by a surgical robot. The passive end effector 1900 further includes a first link segment 1910 and a second link segment 1920. The first link segment 1910 extends between a rotatable connection to the base 1902 and a rotatable connection to one end of the second link segment 1920. Another end of the second link segment 1920 is rotatably connected to a tool attachment mechanism. The rotational axes q1, q2 and q3 are parallel to each other so as to provide a planar cutting plane for the blade 1242. Thus, the 3 DOF motion of the saw 1240 includes x-direction Tx, y-direction Ty and rotational direction about z-axis Rz. One or more of the rotatable connections disclosed for this embodiment may be pivot joints allowing 1 DOF motion, universal joints allowing 2 DOF motions, or ball joints allowing 3 DOF motions.

The tracking markers 52 attached to the end effector base 1902 and the saw 1240 along with the tracking markers on the bones (e.g., tibia and femur) can be used to precisely and continuously monitor the real-time location of the blade 1242 and blade tip relative to the patient bone being cut. Although not explicitly shown in other figures, the tracking markers can be attached to the saw 1240 and all end effectors 1902 in all embodiments to track the location of the blade relative to the patient bone being cut. Although not shown, alternatively or in addition to the tracking markers, encoders can be positioned in each of the link segments 1910 and 1920 to determine precisely where the saw blade tip is at all times.

Example Surgical Procedure

An example surgical procedure using the surgical robot 4 in an Operating Room (OR) can include:

Optional step: surgery is pre-operatively planned based on medical images

1. The surgical robot 4 system is outside the Operating Room (OR). The nurse brings the system to the OR when patient is being prepared for the surgery.
2. The nurse powers on the robot and deploys the robot arm. Nurse verifies precision of robotic and tracking systems
3. In the case of a sterilized passive end effector, the scrub nurse puts a sterile drape on the robot arm and mounts the passive end effector with the sagittal saw on the robot arm. The scrub nurse locks the passive end effector with a lock mechanism. Scrub nurse attached DRAs to passive structure through the drape (if necessary). For a non-sterilized passive end effector, the drape is placed after attachment of the passive end effector on the robot arm, the DRAs are attached to the passive end effector with the drape intervening therebetween, and a sterile saw is attached to the passive end effector with the drape intervening therebetween.
4. The surgeon attaches navigation markers to the patient's bone(s), e.g., tibia and femur. The bones are registered with the camera tracking system 6 using, e.g., Horn algorithm, surface matching or other algorithms. A soft-tissue balance assessment may be performed, whereby the system allows surgeon to assess balance of soft tissue in the operating room, e.g., by tracking relative movement of femur and tibia when surgeon applies forces in different directions (e.g. *varus*/valgus stress). Soft-tissue balance information can be used to alter surgical plan (e.g. move implant parts, change implant type etc.).

5. When surgeon is ready to cut the bone, the scrub nurse brings the surgical robot 4 to the operating table close to the knee to be operated and stabilizes the surgical robot 4 on the floor. The system may operate to guide nurse in finding robot 4 position so that all cut planes are in robot and passive structure workspace.
6. The surgeon selects on the screen of the surgical robot 4 the different parameters according to the planning of the surgery to do the first cut (bone to be cut, cutting plan desired, etc.).
7. The surgical robot 4 automatically moves the robot arm 22 to reposition the passive end effector so the cutting plane of the saw blade becomes aligned with the target plane and the saw blade becomes positioned a distance from the anatomical structure to be cut that is within the range of movement of the tool attachment mechanism of the passive end effector.
8. The surgeon unlocks the passive end effector.
9. The surgeon performs the cut constrained to the cutting plane provide by the passive end effector. The surgical robot 4 may provide real-time display of the tracked location of the saw blade relative to bone so the surgeon can monitor progress of bone removal. In one way, the tracking subsystem processes in real-time the location of the saw relative to the bone based on camera images and various tracking markers attached to the saw, robot arm, end effector, femur and tibia. The surgeon can then lock the passive end effector using the lock mechanism upon completion of the cut.
10. The surgeon selects on the screen the next cut to be executed and proceeds as before.
11. The surgeon may perform a trial implant placement and intermediate soft-tissue balance assessment and based thereon may change the implant plan and associated cuts.
12. Following completion of all cuts, the nurse removes the surgical robot 4 from the operating table and unmounts the passive end effector from the robot arm.
13. The surgeon places the implants and finishes the surgery.

In step 9 above, a physician may have a difficult time to visually confirm the progress of the cut due to tissue and ligaments around the bone and debris being created from the cut, and other surgical instruments near the bone. Even if the visual confirmation may be acceptable, there are areas of the bone the physician cannot see such as the posterior portion of the bone being cut.

Advantageously, one robotic system embodiment of the present invention provides a way for the physician to confirm the progress of the bone being cut in multiple dimensions. The camera tracking system 6 along with the tracking markers attached to the end effector base (1100, 1202, 1302, 1402, 1502, 1602, 1702, 1802, 1902), robotic arm 20 and saw (1140, 1240) allows the tracking subsystem 830 and the computer subsystem 820 to calculate in real-time the precise position of the saw blade relative to bone so the surgeon can monitor progress of bone removal.

Figure 20:
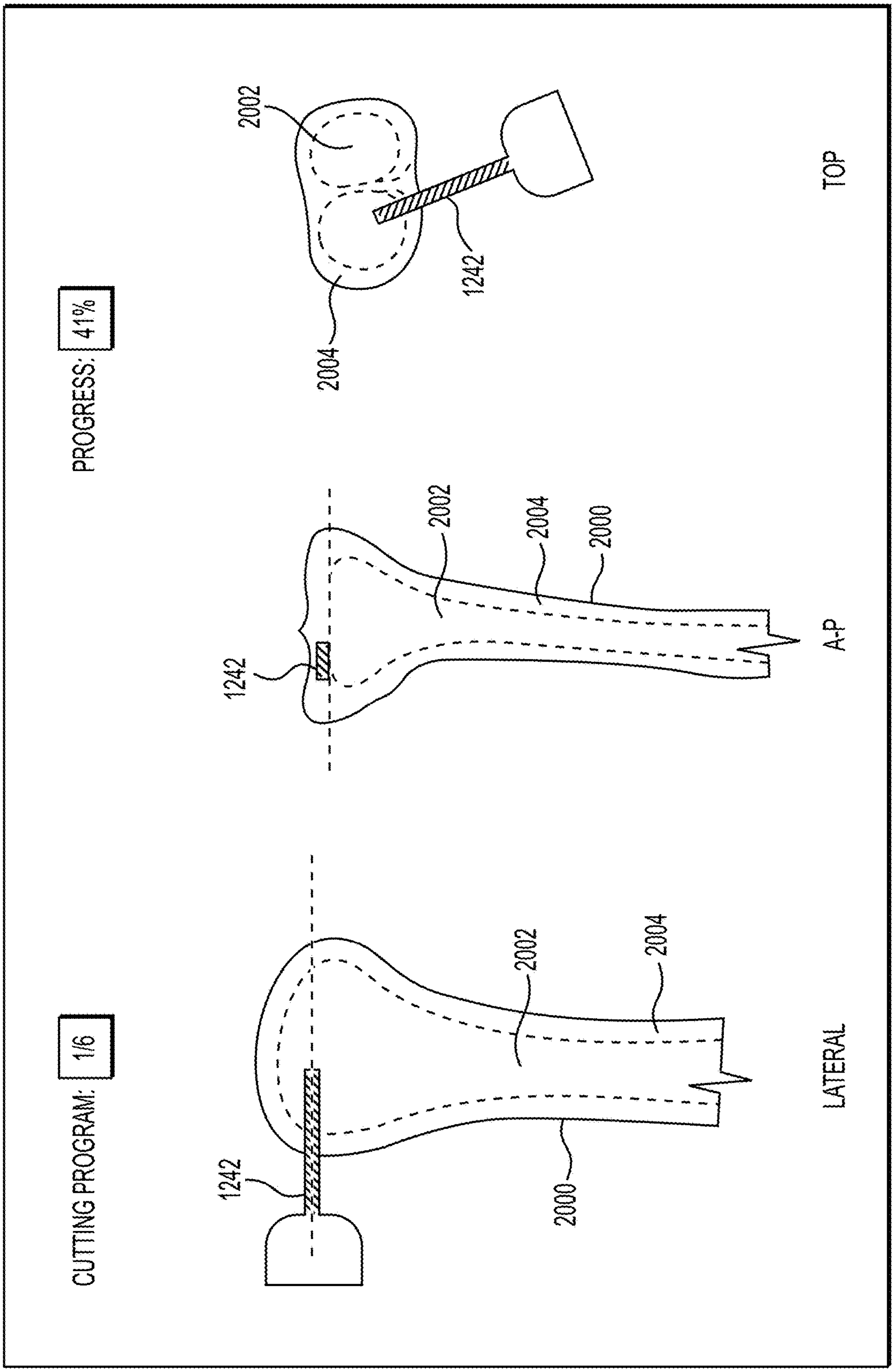
FIG. 20 is a screenshot of a display showing the progress of bone cuts during a surgical procedure.

FIG. 20 is a screenshot of a display showing the progress of bone cuts during a surgical procedure. FIG. 20 shows the subsystems 830 and 820 displaying three images: lateral, A-P and top views. In each image, the real-time location of the saw blade 1242 relative to the bone (e.g., tibia 2000) is displayed on the display 34. The lateral and top views can be especially useful for the physician as they display the saw blade position which cannot be easily seen. At the top portion of the display, the computer subsystem 830, 820 displays the number of cutting programs and what program it is currently running. For example as the screenshot shows, the physician may have programmed 6 planar cuts and the current cutting program is the first one. Also, because the subsystems 830 and 820 can track with tracking markers where the blade may have travelled, it can determine how much of the bone cutting (area that was cut) for a particular cutting program has been completed and the percentage of progress is displayed in the display 34. The bone image itself is preferably derived from actual images of the patient's body for a more accurate representation. The bone image is augmented by the subsystem 820 with a contour line that shows the cortical bone 2004 and spongy bone 2002. This can be important for a physician as the amount of resistance to cutting varies greatly between the two types of bones.

If an augmented reality (AR) head-mounted display is used, the computer subsystem 820 can generate the same contour line showing the cortical and spongy bones and superimpose it over the actual leg continuously as the physician moves his/her head. The area that has been already cut can be overlaid over the actual bone in a dark shade. Moreover, the implant to be inserted over the cut area can also be overlaid on the bone to show the physician that the cutting is being done correctly along the plane of the implant. This is all possible because the subsystems 830 and 820 can track the position of the blade and history of its movement relative to the bone with the tracking markers and the camera subsystem.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A surgical system comprising:

a tracking system configured to determine a pose of an anatomical structure that is to be cut by a saw blade and to determine a pose of the saw blade;

a surgical robot including a robot base, a robot arm connected to the robot base, at least one motor operatively connected to move the robot arm relative to the robot base, a passive end effector including a base configured to attach to an end effector coupler of the robot arm, a first mechanism that extends between a rotatable connection to the base and a rotatable connection to a tool attachment mechanism, and a second mechanism that extends between a rotatable connection to the base and a rotatable connection to the tool attachment mechanism, the first and second mechanisms pivot about the rotatable connections to constrain movement of the tool attachment mechanism to a range of movement within a working plane, the tool attachment mechanism is configured to connect to the surgical saw comprising a saw blade for cutting, and at least one controller connected to the at least one motor and configured to determine a pose of a target plane based on a surgical plan defining where the anatomical structure is to be cut and based on the pose of the anatomical structure; and generate steering information based on comparison of the pose of the target plane and the pose of the surgical saw, wherein the steering information indicates where the passive end effector needs to be moved so the cutting plane of the saw blade becomes aligned with the target plane and the saw blade becomes positioned a distance from the anatomical structure to be cut that is within the range of movement of the tool attachment mechanism of the passive end effector.

2. The surgical system of claim 1, wherein the at least one controller is further configured to control movement of the at least one motor based on the steering information to reposition the passive end effector so the cutting plane of the saw blade becomes aligned with the target plane and the saw blade becomes positioned the distance from the anatomical structure to be cut that is within the range of movement of the tool attachment mechanism of the passive end effector.

3. The surgical system of claim 1, wherein the at least one controller is further configured to provide the steering information to a display device for display to guide operator movement of the passive end effector so the cutting plane of the saw blade becomes aligned with the target plane and so the saw blade becomes positioned the distance from the anatomical structure, which is to be cut, that is within the range of movement of the tool attachment mechanism of the passive end effector.

4. The surgical system of claim 3, wherein the at least one controller is further configured to configure the steering information for display on a head-mounted display device having a see-through display screen that displays the steering information as an overlay on the anatomical structure that is to be cut to guide operator movement of the passive end effector so the cutting plane of the saw blade becomes aligned with the target plane and the saw blade becomes positioned the distance from the anatomical structure within the range of movement of the tool attachment mechanism of the passive end effector.

5. The surgical system of claim 4, wherein to configure the steering information for display on the head-mounted display device the at least one controller generates a graphical representation of the target plane that is displayed as an overlay anchored to and aligned with the anatomical structure that is to be cut, and generates another graphical representation of the cutting plane of the saw blade that is displayed as an overlay anchored to and aligned with the saw blade.

6. The surgical system of claim 4, wherein to configure the steering information for display on the head-mounted display device the at least one controller generates a graphical representation a depth of cut made by the saw blade into a graphical representation of the anatomical structure being cut.

7. The surgical system of claim 1, wherein the tracking system is configured to determine the pose of the anatomical structure that is to be cut by the saw blade based on determining a pose of tracking markers that are attached to the anatomical structure, and is configured to determine a pose of the surgical saw based on determining a pose of tracking markers on at least one of the surgical saw and the passive end effector.

8. The surgical system of claim 1, wherein the tracking system is configured to determine the pose of the surgical saw based on rotary position sensors configured to measure rotational positions of the first and second mechanisms during movement of the tool attachment mechanism within the working plane.

9. The surgical system of claim 1, wherein:

the first mechanism includes first and second link segments, the first link segment extends between a rotatable connection to a first location on the base and a rotatable connection to an end of the second link segment;

the second mechanism includes third and fourth link segments, the third link segment extends between a rotatable connection to a second location on the base and a rotatable connection to an end of the fourth link segment, wherein the first and second locations on the base are spaced apart on opposite sides of a rotational axis of the base when rotated by the robot arm; and the tool attachment mechanism includes a fifth link segment that extends between rotatable connections to distal ends of the second and fourth link segments from the base.

10. The surgical system of claim 1, wherein:

the first mechanism includes first and second link segments, the first link segment extends between a rotatable connection to a first location on the base and a rotatable connection to an end of the second link segment; and the second mechanism includes third and fourth link segments, the third link segment extends between a rotatable connection to a second location on the base and a rotatable connection to an end of the fourth link segment, wherein the first and second locations on the base are spaced apart on opposite sides of a rotational axis of the base when rotated by the robot arm, wherein distal ends of the second and fourth link segments from the base are rotatably connected to each other and to the tool attachment mechanism.

11. The surgical system of claim 1, wherein:

the base includes first and second elongated base segments that extend from spaced apart locations on opposite sides of a rotational axis of the base when rotated by the robot arm, and the first and second elongated base segments extend in a direction away from the end effector coupler of the robot arm when attached to the passive end effector;

the first mechanism includes first, second, third, and fourth link segments, the first and second link segments extend parallel to each other between rotatable connections to spaced apart locations on the first elongated base segment and spaced apart locations on the third link segment, an end of the third link segment is rotatably connected to an end of the fourth link segment;

the second mechanism includes fifth, sixth, and seventh link segments, the fifth and sixth link segments extend parallel to each other between rotatable connections to spaced apart locations on the second elongated base segment and spaced apart locations on the seventh link segment; and the tool attachment mechanism includes an eighth link segment that extends between rotatable connections to distal ends of the fourth and seventh link segments from the base.

12. The surgical system of claim 11, wherein:

the eighth link segment of the tool attachment mechanism includes an attachment member that extends in a direction away from the base to a rotatable connector that is configured to connect to the surgical saw, wherein the attachment member extends from a location on the eighth link segment that is closer to the fourth link segment than to the seventh link segment.

13. The surgical system of claim 1, wherein:

the first mechanism includes a first link segment;

the second mechanism includes a second link segment;

the tool attachment mechanism includes third, fourth, fifth, sixth, and seventh link segments;

the first and second link segments extend between rotatable connections to first and second locations, respectively, on the base to rotatable connections at opposite ends of the third link segment, wherein the first and second locations on the base are spaced apart on opposite sides of a rotational axis of the base when rotated by the robot arm;

the fourth link segment extends from the third link segment in a direction towards the base; and the fifth and sixth link segments extend parallel to each other between rotatable connections to spaced apart locations on the fourth link segment and spaced apart locations on the seventh link segment, wherein the seventh link segment includes a rotatable connector that is configured to connect to the surgical saw.

14. The surgical system of claim 1, wherein:

the first mechanism includes a first link segment;

the second mechanism includes a second link segment;

the tool attachment mechanism includes third, fourth, fifth, sixth, and seventh link segments;

the first and second link segments extend between rotatable connections to first and second locations, respectively, on the base to rotatable connections at opposite ends of the third link segment, wherein the first and second locations on the base are spaced apart on opposite sides of a rotational axis of the base when rotated by the robot arm;

the fourth link segment extends from the third link segment in a direction away from the base; and the fifth and sixth link segments extend parallel to each other between rotatable connections to spaced apart locations on the fourth link segment and spaced apart locations on the seventh link segment, wherein the seventh link segment includes a rotatable connector that is configured to connect to the surgical saw.

15. The surgical system of claim 1, wherein:

the first mechanism includes first and second link segments, the first link segment extends between a rotatable connection to the base and a rotatable connection to an end of the second link segment;

the second mechanism includes a third link segment;

the tool attachment mechanism includes a fourth link segment, the second and third link segments extend away from the base and parallel to each other between rotatable connections to spaced apart locations on the first link segment and spaced apart locations on the fourth link segment; and the fourth link segment includes an attachment member that extends in a direction away from the base to a rotatable connector that is configured to connect to the surgical saw, wherein the attachment member extends from a location on the fourth link segment that is closer to the third link segment than to the second link segment.

16. The surgical system of claim 1, wherein:

the first mechanism includes a first link segment;

the second mechanism includes a second link segment;

the tool attachment mechanism includes a third link segment;

the first and second link segments extend between rotatable connections to first and second locations, respectively, on the base to rotatable connections at opposite ends of the third link segment, wherein the first and second locations on the base are spaced apart on opposite sides of a rotational axis of the base when rotated by the robot arm;

the third link segment includes an attachment member that extends in a direction away from the base to a rotatable connector that is configured to connect to the surgical saw, wherein the attachment member extends from a location on the third link segment that is closer to the first link segment than to the second link segment.

17. A surgical system comprising:

a tracking system configured to determine a pose of an anatomical structure that is to be cut by a saw blade and to determine a pose of the saw blade;

a surgical robot including a robot base, a robot arm connected to the robot base, at least one motor operatively connected to move the robot arm relative to the robot base, a passive end effector including a base configured to attach to an end effector coupler of the robot arm, a first mechanism that extends between a rotatable connection to the base and a rotatable connection to a tool attachment mechanism, and a second mechanism that extends between a rotatable connection to the base and a rotatable connection to the tool attachment mechanism, the first and second mechanisms pivot about the rotatable connections to constrain movement of the tool attachment mechanism to a range of movement within a working plane, the tool attachment mechanism is configured to connect to the surgical saw comprising a saw blade for cutting, and at least one controller connected to the at least one motor and configured to determine a pose of a target plane based on a surgical plan defining where the anatomical structure is to be cut and based on the pose of the anatomical structure; and generate steering information based on comparison of the pose of the target plane and the pose of the surgical saw.

18. The surgical system of claim 17, wherein the at least one controller is further configured to control movement of the at least one motor based on the steering information to reposition the passive end effector so the cutting plane of the saw blade becomes aligned with the target plane and the saw blade becomes positioned the distance from the anatomical structure to be cut that is within the range of movement of the tool attachment mechanism of the passive end effector.

19. The surgical system of claim 18, wherein the at least one controller is further configured to provide the steering information to a display device for display to guide operator movement of the passive end effector so the cutting plane of the saw blade becomes aligned with the target plane and so the saw blade becomes positioned the distance from the anatomical structure, which is to be cut, that is within the range of movement of the tool attachment mechanism of the passive end effector.

20. The surgical system of claim 19, wherein the at least one controller is further configured to configure the steering information for display on a head-mounted display device having a see-through display screen that displays the steering information as an overlay on the anatomical structure that is to be cut to guide operator movement of the passive end effector so the cutting plane of the saw blade becomes aligned with the target plane and the saw blade becomes positioned the distance from the anatomical structure within the range of movement of the tool attachment mechanism of the passive end effector.

* * * * *